United States Patent
Iyer

(10) Patent No.: US 10,391,166 B2
(45) Date of Patent: Aug. 27, 2019

(54) SHORT OLIGONUCLEOTIDES AS VACCINE ADJUVANTS AND THERAPEUTIC AGENTS

(71) Applicant: SPRING BANK PHARMACEUTICALS, INC., Milford, MA (US)

(72) Inventor: Radhakrishnan P. Iyer, Shrewsbury, MA (US)

(73) Assignee: SPRING BREAK PHARMACEUTICALS, INC., Milford, MA (US)

( * ) Notice: Subject to any disclaimer, the term of this patent is extended or adjusted under 35 U.S.C. 154(b) by 0 days.

(21) Appl. No.: 14/767,113

(22) PCT Filed: Feb. 18, 2014

(86) PCT No.: PCT/US2014/016996
§ 371 (c)(1),
(2) Date: Aug. 11, 2015

(87) PCT Pub. No.: WO2014/127378
PCT Pub. Date: Aug. 21, 2014

(65) Prior Publication Data
US 2015/0374816 A1    Dec. 31, 2015

Related U.S. Application Data

(60) Provisional application No. 61/766,011, filed on Feb. 18, 2013.

(51) Int. Cl.
| | | |
|---|---|---|
| *C07H 21/04* | (2006.01) | |
| *A61K 39/39* | (2006.01) | |
| *A61K 31/7084* | (2006.01) | |
| *A61K 31/7088* | (2006.01) | |
| *A61K 39/04* | (2006.01) | |
| *A61K 39/00* | (2006.01) | |

(52) U.S. Cl.
CPC .......... *A61K 39/39* (2013.01); *A61K 31/7084* (2013.01); *A61K 31/7088* (2013.01); *A61K 39/04* (2013.01); *A61K 2039/55561* (2013.01); *A61K 2039/58* (2013.01); *A61K 2039/585* (2013.01)

(58) Field of Classification Search
CPC .................................................... A61K 48/00
See application file for complete search history.

(56) References Cited

FOREIGN PATENT DOCUMENTS

WO    2012030626 A2    3/2012

OTHER PUBLICATIONS

C. da Costa et al. (International J of Infectious Diseases 2015: 5-12, p. 10).*
Awate et al., "Mechanisms of action of adjuvants", Frontiers in Immunology, vol. 4, 2013.
Extended European Search Report from European Application No. 14750982.2 dated Jul. 20, 2016.
Sabbah et al., "Activation of innate immune antiviral responses by Nod2", Nature Immunology, vol. 10. No. 10, 2009, pp. 1073-1080.
Jin et al. "Synthesis and Antiviral Evaluation of Nucleic Acid-Based (NAB) Libraries," Bioorganic & Medical Chemistry Letters, 2000, 10:1921-1925.
Mertes et al. "Synthesis of carbonate analogs of dinucleosides. 3'-thymidinyl 5'-thymidinyl carbondate, 3'-thymidinyl 5'-(5-fluoro-2'-deoxyuridinyl) carbonate, and 3'-(5-fluoro-2'-deoxyuridinyl) 5'thymidinyl carbonate," Journal of Medicinal Chemistry, 1969, 12:154-157.
Uhlmann et al. "Antisense oligo nucleotides: A new therapeautic principle," Chemical Reviews, 1990, 90(4):544-584.

* cited by examiner

*Primary Examiner* — Kimberly Chong
(74) *Attorney, Agent, or Firm* — Goodwin Procter LLP

(57) ABSTRACT

The invention provides a method of treating a microbial infection in a subject and a method of improving an immune system response in a subject against a disease, condition, infection, or virus thereof, by administering an effective amount of a nucleoside, short oligonucleotide compound or an analog thereof, or a pharmaceutically acceptable salt, racemate, enantiomer, diastereomer, geometric isomer, or tautomer thereof. In addition, the invention provides methods for treating or preventing a viral infection, bacterial infection, parasitic infection, or fungal infection in a subject (such as, a human). The compounds of the invention include, for example, di-, and trinucleotide compounds as provided herein. The compounds of the invention are useful for different therapeutic applications including, such as, prophylactics and therapeutics. The invention also provides design and synthesis of a compound that is useful for various therapeutic applications as mentioned herein.

2 Claims, 17 Drawing Sheets

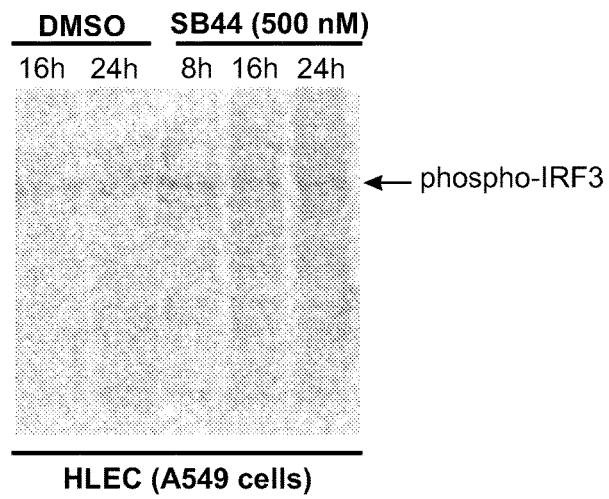

FIG. 5

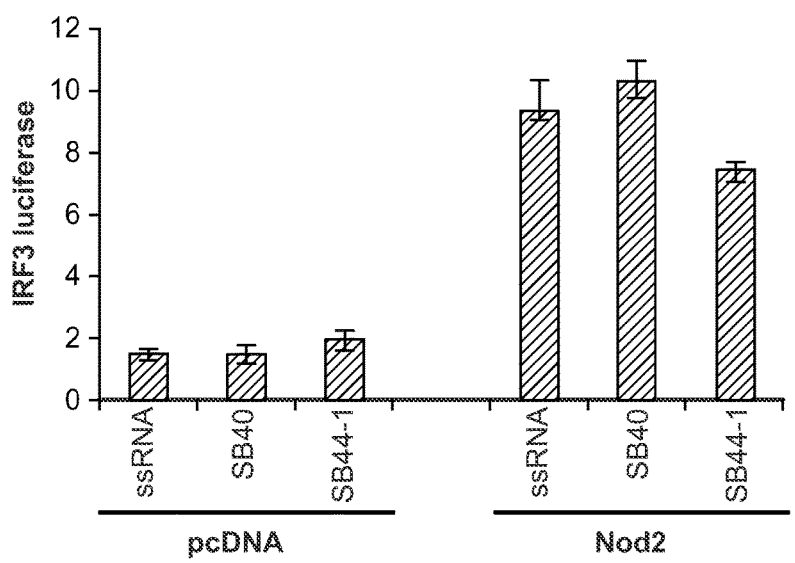

Induction of antiviral response by SMNH compounds (SB 40 and SB 44) via NOD2 activation. HEK 293 cells were transfected with NOD2, pcDNA and IRF3-luciferase. The cells were then incubated with ssRNA (0.5 mg/ml) or SMNH compounds (1 μM). Following 12 h incubation, Luciferase activity was measured as described previously. The Luciferase assay results are presented as mean ± S.D. from three independent experiments.

FIG. 6

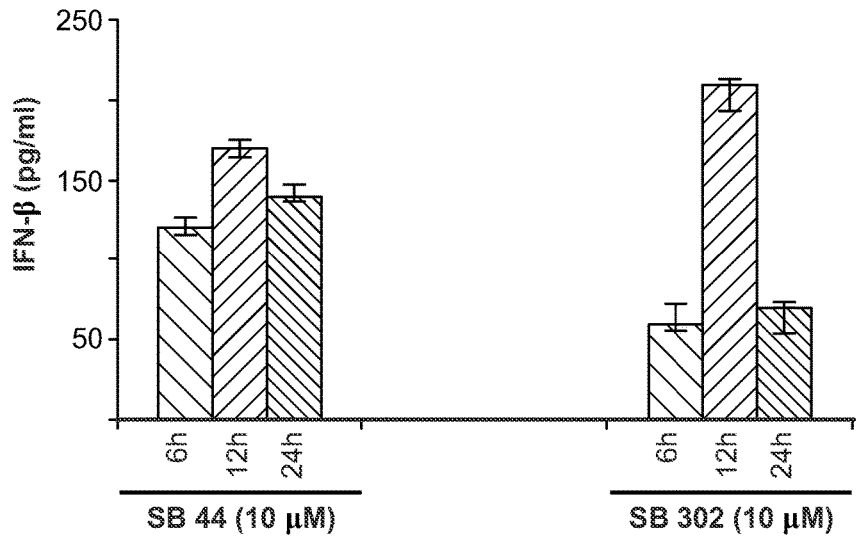

SMNH compounds (SB 44 and SB 302) induces production of interferon-β (IFN-β) from human lung epithelial A549 cells. The cells were incubated with SMNH compounds SB 44 (10 µM) and SB 302 (10 µM). Following 6h, 12h, 24h incubation, medium supernatant was collected to detect IFN-β by ELISA. The values obtained with DMSO (at 6h, 12h, or 24h post-treatment) were subtracted from the corresponding values obtained from SMNH compound treated cells.

FIG. 7

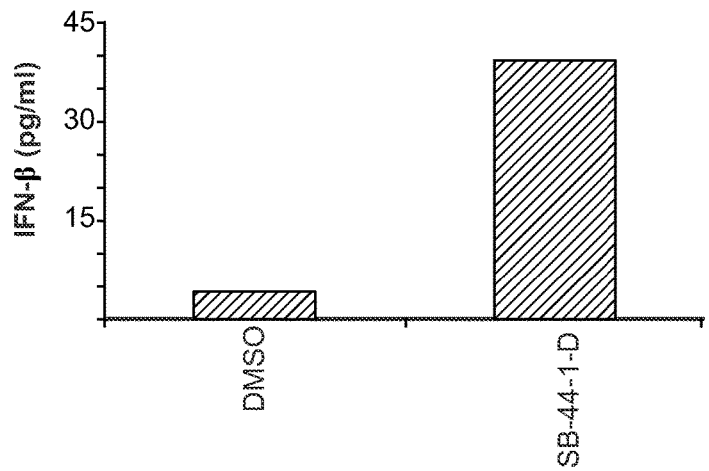

SB-44-1-D treatment results in production of IFN-β from lung epithelial cells. Human lung epithelial A549 cells were treated with DMSO (vehicle control) or SB-44-1 (10 µM) for 24h. After treatment, ELISA assay was performed with medium supernatant to measure levels of IFN-β released from cells upon treatment. The data represents mean of three independent experiments with similar results. RESULT – SB-44-1-D treatment triggers IFN-β release from lung epithelial cells.

FIG. 8

Induction of innate immune responder genes by SB-44-1-D. Human lung epithelial A549 cells were treated with DMSO (vehicle control), SB-50 (10 μM) or SB-44-1 (10 μM) for 12h. After treatment, RNA collected from the cells were utilized for RT-PCR analysis to detect expression of RIG-I, Nod2 and interferon-β (IFN-β) genes. RESULT – SB-44-1-D induces expression of RIG-I, Nod2 and IFN-β genes in A549 cells.

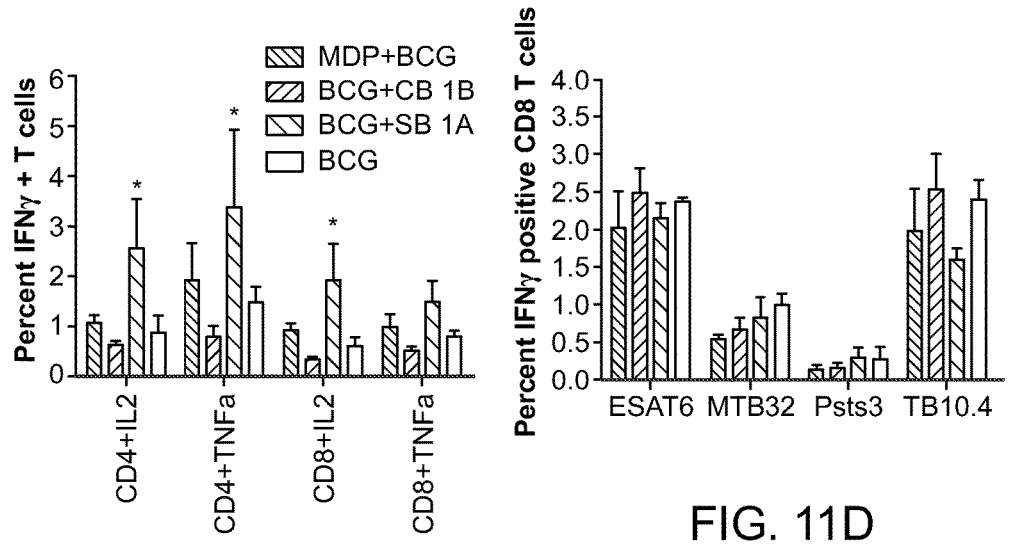
FIG. 11C
FIG. 11D
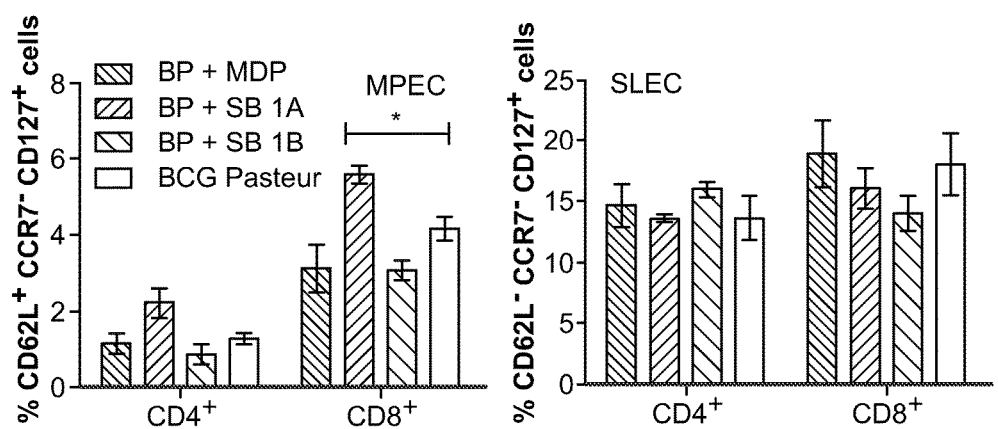
FIG. 11E

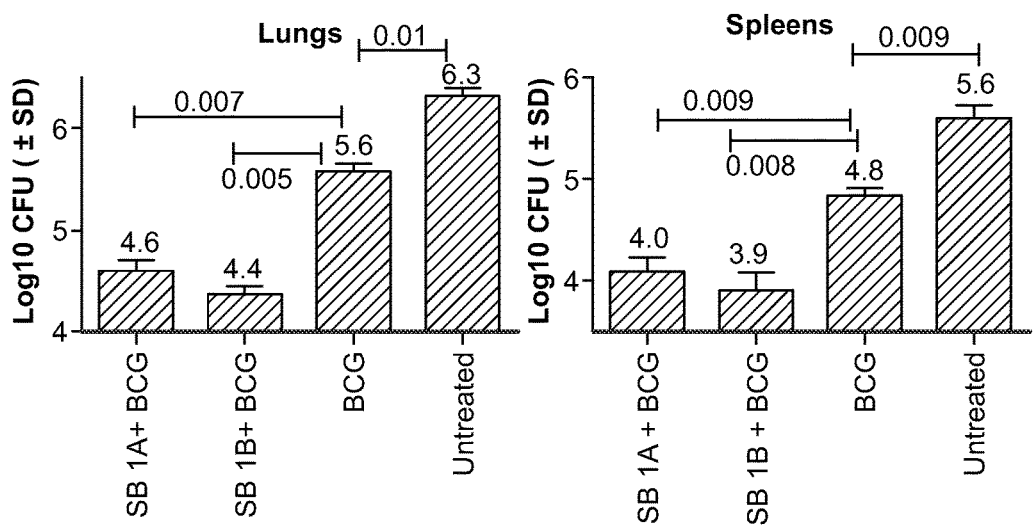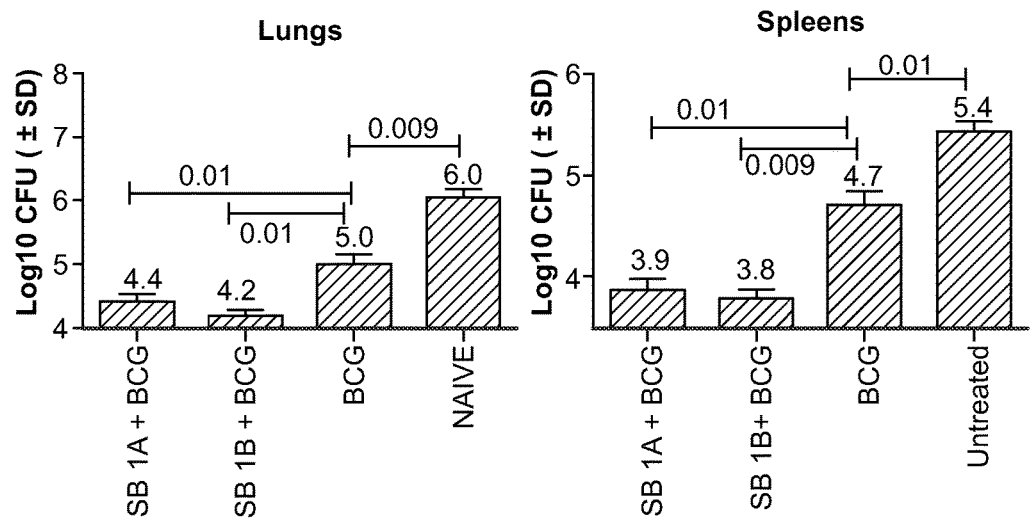
FIG. 15

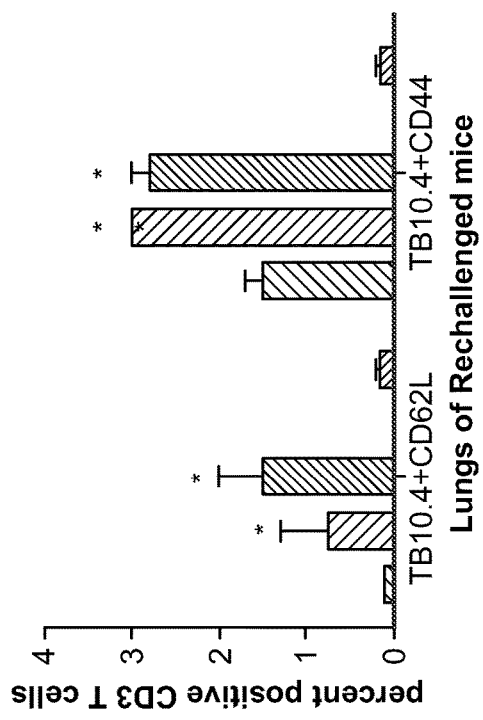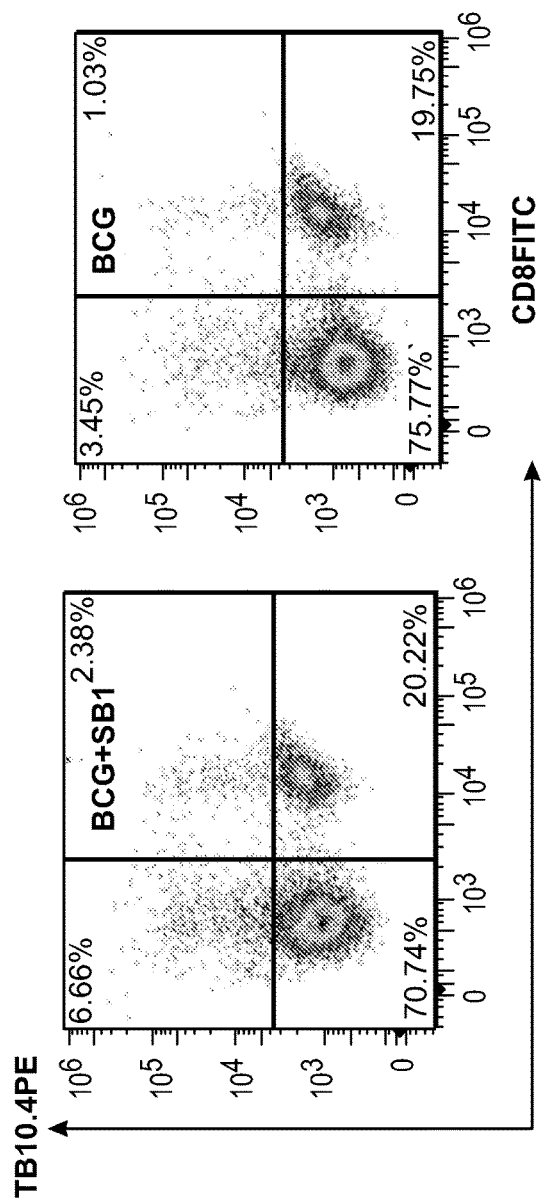
FIG. 16D

SHORT OLIGONUCLEOTIDES AS VACCINE ADJUVANTS AND THERAPEUTIC AGENTS

CROSS-REFERENCE TO RELATED APPLICATION

The subject invention is a national stage application under 35 U.S.C. § 371 of International Application No. PCT/US2014/016996, filed Feb. 18, 2014, published as International Publication No. WO2014/127378 on Aug. 21, 2014, which claims the benefit of priority from U.S. Provisional Patent Application Ser. No. 61/766,011, filed Feb. 18, 2013, the disclosure of each of which is herein incorporated by reference in its entirety.

BACKGROUND OF THE INVENTION

Innate immunity plays a critical role in the body's defense against prokaryotic and eukaryotic pathogens such as viruses, bacteria, fungii, parasites etc. Indeed, acute and chronic infections caused by viruses constitute a major worldwide public health crisis with significant unmet medical need (1,2). In addition to infectious diseases, viruses cause 15-20% of all cancers worldwide including liver, cervical, and pancreatic cancers, each resulting in significant mortalities and morbidities.

In addition to human suffering, viral diseases result in overwhelming healthcare costs and loss of productivity. For example, worldwide 500 to 600 million people are chronically infected with HBV and HCV, and 1 to 2 million deaths occurs every year due to virus-induced liver cirrhosis and liver cancer. Tens of thousands of patients worldwide are in desperate need of liver transplantation. Human papilloma virus infection leads to cervical cancer and incidence of Kaposi sarcoma associated with HIV infection is all well documented. Pandemic influenza is characterized by high levels of morbidity and mortality in humans, and associated with increased levels of infection and pathogenesis due to the lack of pre-existing immunities against its novel antigenic subtype. Antivirals may not only potentially slow the spread of pandemic influenza, but may ultimately be a solution. Tuberculosis caused by *Mycobacterium tuberculosis* (Mtb) kills more people today than any other bacterial infection. Nearly a third of human population, in over 90 countries, is infected with Mtb and 2 million people die each year from the disease.

Although vaccines are available as prophylactic against a limited number of viruses, they have no real therapeutic benefit for those already infected. Moreover, vaccines against certain viruses (e.g., influenza vaccines) are unlikely to make a significant impact on mortality in a pandemic because of the time required to generate enough doses of a suitable vaccine against the new human strain after it has been identified. Use of adjuvants can augment the potency of vaccines and afford protection against broad range of viruses.

Consequently, our antiviral defense almost exclusively relies on the use of antiviral drugs. Unfortunately, many medically important viruses, particularly RNA viruses are dangerous, cannot be tested in model systems, or cannot be propagated for testing of potential candidate drugs.

Many of the current antiviral drugs have been developed as viral polymerase, protease, integrase, and entry inhibitors. However, drugs designed to inhibit viral growth can also adversely affect host cells since viral life cycle engages normal host cellular functions. The limited viral targets that are amenable to antiviral intervention further compound antiviral drug discovery. Consequently, despite almost 50 years of antiviral research, our arsenal of antiviral drugs remain dangerously small with only about 34 antiviral drugs in the world market, mostly against HIV and Herpes viruses.

Further, the current treatment options for several chronic viral diseases including HCV and HBV remain extremely limited and challenging. Indeed, viral rebound upon cessation of therapy, drug-induced toxicity, and emergence of resistant strains under selective pressure of antiviral drugs continue to remain serious problems in current antiviral therapy. Complete eradication of the virus is rarely achieved, and at best in a very small cohort of patients, because current antiviral therapy produces inadequate and unsustainable antiviral response. The developments of drugs that target host-encoded functions provide an alternate strategy for antimicrobial discovery.

Viruses have also continuously evolved clever strategies to evade host immune response and to develop resistance to drugs through a variety of mechanisms. Cells protect themselves from microbial infections via the cellular sensors including Retinoic acid inducible gene (RIG-I) and other RIG-like proteins (RLRs), MDA5, nucleotide oligomerization domain protein-2 (NOD2 and other Nod-like proteins (NLRs). Activation of these proteins via the interaction of pathogen recognition receptors with the microbial nucleic acid or peptides cause the Interferon signaling pathway resulting in IFN production that protects cells from infections. Indeed, it is being recognized that both DNA and RNA viruses inhibit type I Interferon (IFN) production thereby suggesting that controlling the IFN response is essential for the survival of a broad range of viruses (3,4). Thus, the development of effective antiviral therapies must involve the use of combinations of new classes of drugs each with novel, multiple mechanisms of action including those that stimulate host immune response for eradication of the virus. Similarly, bacteria have evolved unique mechanisms that result in resistance to antibacterial agents. Thus, the development of effective antibacterial therapies must involve the use of combinations of new classes of drugs each with novel, multiple mechanisms of action including those that stimulate host immune response for eradication of the bacteria. Many different types of cancers have evolved different mechanisms to develop resistance to anticancer agents. Thus, the development of effective anti-cancer therapies must involve the use of combinations of new classes of drugs each with novel, multiple mechanisms of action including those that stimulate host immune response for eradication of cancer.

SUMMARY OF THE INVENTION

In one aspect, the invention provides nucleosides, short oligonucleotide compounds, or analogs thereof, or pharmaceutically acceptable salts, racemates, enantiomers, diastereomers, geometric isomers, or tautomers thereof (hereinafter referred to as "the compounds of the invention") that are useful as prophylactic agents. In another aspect, the invention provides nucleosides, short oligonucleotide compounds, or analogs thereof, or pharmaceutically acceptable salts, racemates, enantiomers, diastereomers, geometric isomers, or tautomers thereof that are useful as vaccine adjuvants.

The compounds of the invention include, such as, the compounds of formula (I):

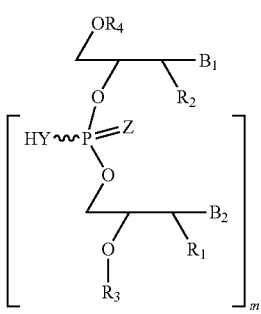

or pharmaceutically acceptable salts, racemates, enantiomers, diastereomers, geometric isomers, or tautomers thereof, wherein:

$R_1$ and $R_2$ are each independently, H, OH, O-akyl, alkyl, substituted alkyl, cycloalkyl, aryl, substituted aryl, aralkyl, heterocyclic, O-aryl, O-heteroarylaryl, or heterocyclic;

$R_3$ is selected from hydrogen, alkyl, substituted alkyl, C(O)-alkyl, C(O)O-alkyl, C(O)-aryl, C(O)O-aryl, C(O)NH-alkyl, and C(O)NH-aryl;

Y and Z are each independently, O or S;

$B_1$ and $B_2$ are each independently adenine, guanine, thymine, cytosine, uracil or modified nucleosides;

m=1 to 6.

$R_4$ is independently H, alkyl, substituted alkyl, C(O)-alkyl, C(O)O-alkyl, C(O)-aryl, C(O)O-aryl, C(O)NH-alkyl, and C(O)NH-aryl, a monophosphate, diphosphate, or triphosphate group.

In one embodiment, a compound of the invention is a compound of formula (II):

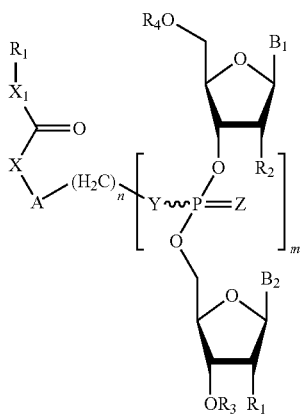

II or a pharmaceutically acceptable salt, racemate, enantiomer, diastereomer, geometric isomer, or tautomer thereof, wherein:

X=absent, O, NH, NR, or S;

$X_1$=absent, O, or NH;

A=absent, aryl, or aralkyl;

n=0, 1, 2, 3, 4, or 5;

R=alkyl, substituted alkyl, cycloalkyl, aryl, substituted aryl, aralkyl, heterocyclic, O-alkyl, O-heteroaryl, or steroidal;

$R_1$ and $R_2$ are each independently, H, OH, O-akyl, alkyl, substituted alkyl, cycloalkyl, aryl, substituted aryl, aralkyl, heterocyclic, O-aryl, O-heteroarylaryl, or heterocyclic;

$R_3$ is selected from hydrogen, alkyl, substituted alkyl, C(O)-alkyl, C(O)O-alkyl, C(O)-aryl, C(O)O-aryl, C(O)NH-alkyl, and C(O)NH-aryl;

Y and Z are each independently, O or S;

$B_1$ and $B_2$ are each independently adenine, guanine, thymine, cytosine, uracil or modified nucleosides;

m=1 to 6;

$R_4$ is independently H, alkyl, substituted alkyl, C(O)-alkyl, C(O)O-alkyl, C(O)-aryl, C(O)O-aryl, C(O)NH-alkyl, and C(O)NH-aryl a monophosphate, diphosphate, or triphosphate group.

In one embodiment, the compound of the invention is a compound of the following structure:

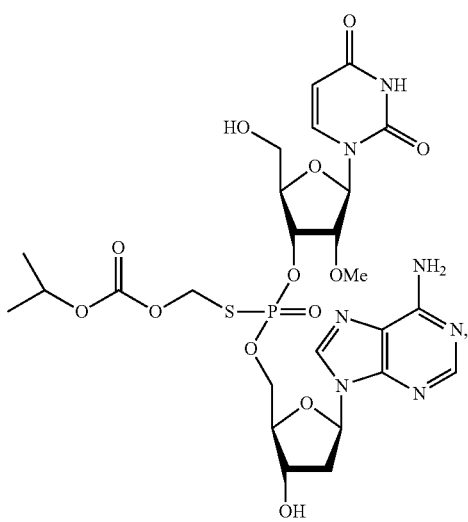

or a pharmaceutically acceptable salt, racemate, enantiomer, diastereomer, geometric isomer, or tautomer thereof.

In another embodiment, the compound of the invention is a compound of the following structure:

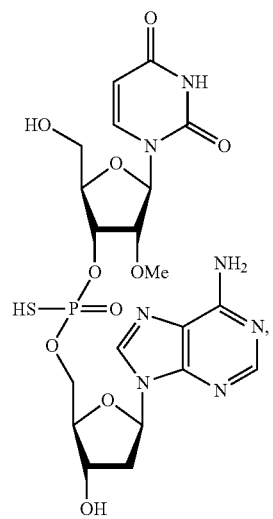

or a pharmaceutically acceptable salt, racemate, enantiomer, diastereomer, geometric isomer, or tautomer thereof.

The invention also provides a method of treating a microbial infection in a subject (or a host) by administering to the subject (or the host) identified as in need thereof an effective amount of a compound of the invention.

In another aspect, the invention provides a method of improving an immune system response in a subject (or a host) against a disease, condition, infection, or virus. The method comprises administering to the subject an effective amount of a compound of the invention as a vaccine adjuvant.

In certain embodiments of the methods, the compound of the invention is a short oligonucleotide compound or analog thereof of formula (I), or a pharmaceutically acceptable salt, racemate, enantiomer, diastereomer, geometric isomer, or tautomer thereof.

In other embodiments, the compound of the invention is a short oligonucleotide compound or analog thereof of formula (II), or a pharmaceutically acceptable salt, racemate, enantiomer, diastereomer, geometric isomer, or tautomer thereof.

In one embodiment, the compound of the invention is

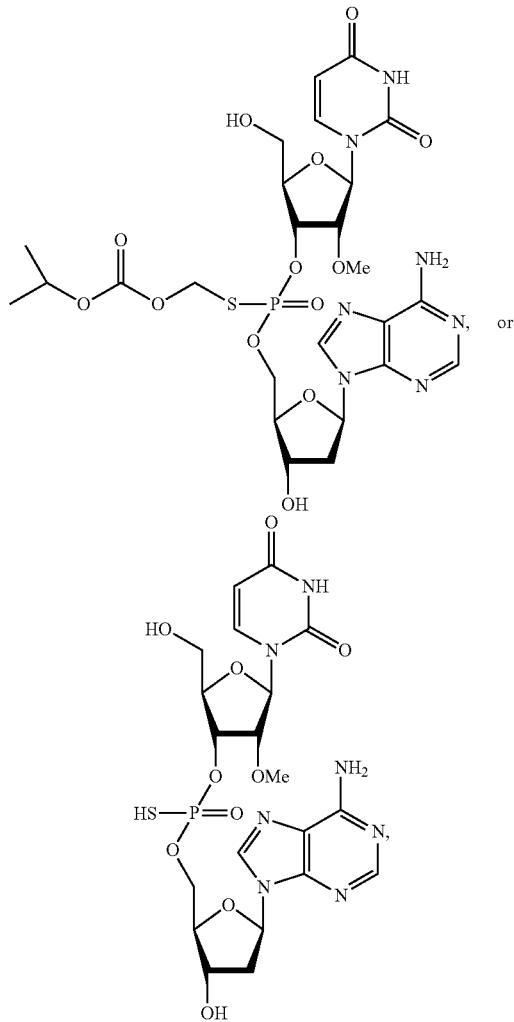

or a pharmaceutically acceptable salt, racemate, enantiomer, diastereomer, geometric isomer, or tautomer thereof.

The invention also provides a method for the prevention and treatment of a viral infection in a host (or subject), including human. The method includes administering an effective amount of a compound of the invention.

In still another aspect, the invention provides a method for the prevention and treatment of a bacterial infection in a host (or subject), including human, comprising administering an effective amount compound of the invention.

Further, the invention provides a method of the prevention and treatment of a parasitic infection in a host (or subject), including human, wherein the method includes administering an effective amount compound of the invention.

Still further, the invention provides a method for the prevention and treatment of a fungal infection in a host (subject), including human, by administering to the host an effective amount compound of the invention.

According to the methods of the invention, a compound of the invention can be administered together with a vaccine (such as, a BCG vaccine) or one or more additional agents. That is, according to the methods of the invention, a compound of the invention can be administered alone or in combination or sequentially with a vaccine or an additional agent (or agents).

In one embodiment, compounds of the invention and the vaccine are administered for treating or preventing a microbial infection.

In another embodiment, compounds of the invention are administered in combination with other antimicrobial agents for treating or preventing a microbial infection.

In another embodiment, the methods and compounds of the invention are used against a virus.

In a further embodiment, the methods and compounds are used for treating or preventing a cancer.

The invention further provides pharmaceutical compositions and kits for the treatment or prevention of a condition, disease, infection, or virus that is delineated herein. The pharmaceutical compositions include a therapeutically effective amount of a compound of the invention, and a pharmaceutically acceptable excipient. The kits of the invention include a therapeutically effective amount of a compound of the invention, and written instructions for administering the compound for the treatment or prevention of the condition, disease, infection, or virus delineated herein. The invention also provides packaged pharmaceuticals and articles for the treatment or prevention of a condition, disease, infection, or virus herein.

Moreover, the invention also provides design and synthesis of a compound that is useful for various therapeutic applications as mentioned herein. Other features and advantages of the invention will be apparent from the detailed description, and from the claims.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 shows that induction of IRF3 results in the formation of the phosphorylated IRF3, a key intermediate in the IFN signaling cascade.

FIG. 6 shows that the IRF3 induction by SB 1B is mediated via NOD2 activation; SB 40 is the active metabolite of SB 44.

FIG. 7 shows that SMNH compounds (SB 44 and SB 302, a, oxalate form) induces production of interferon-β (IFN-β) from human lung epithelial A549 cells.

FIG. 8 shows SB 1B (shown as "SB-44-1-D") treatment results in production of IFN-β from lung epithelial A549 cells.

FIG. 12 shows that NOD2-activating compounds SB 1A (also as SB 44) and SB 1B (the Rp-isomer of SB 44) induce IL-1β only in combination with either MDP or intact BCG bacilli through a caspase-dependent mechanism in macrophages.

FIG. 15 (a-b) shows that SB 1A (also as SB 44) or SB 1B (the Rp-isomer of SB 44) combination with BCG vaccine retain the ability to mount a better recall response against re-challenge with tuberculosis.

DETAILED DESCRIPTION OF THE INVENTION

Figure 1:
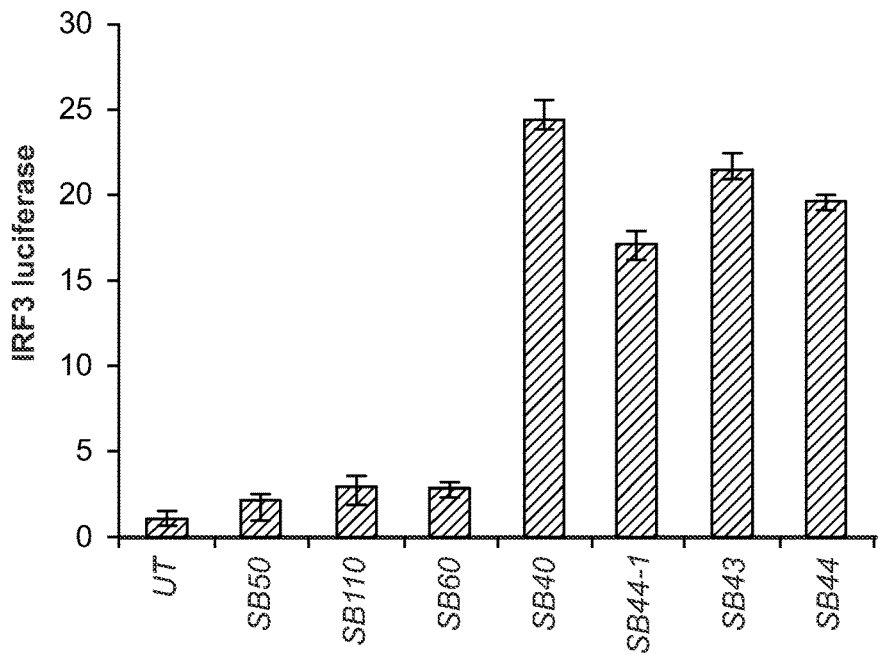
FIG. 1 shows that activation of interferon regulatory factor-3 (IRF3)-luciferase reporter gene in untreated (UT) and SMNH compounds treated Human lung epithelial cells (HLE A549 cells).

In one aspect, the invention features compounds delineated herein and methods of using such compounds for the treatment of a microbial infection in a subject. In another aspect, the invention relates to compounds, compositions, and methods for improving an immune system response in a subject against a disease, condition, infection, or virus.

The invention also provides methods for the prevention and treatment of a viral infection, bacterial infection, parasitic infection, or fungal infection in a host (or a subject), including human, by administering to the host (or subject) an effective amount of a compound of the invention.

The Multi-drug-resistant Mtb (MDR-Mtb), is resistant to many of the current anti-TB drugs including Isoniazid, Rifampin, Kanamycin etc. The WHO estimates that up to 50 million persons worldwide may be infected with MDR-Mtb. Because of the difficulties in drug treatment/resistance, vaccination to prevent or limit tuberculosis is becoming increasingly important. Currently, BCG vaccine is only variably protective against childhood TB, and does not offer protection against adult disease. Thus, more potent BCG vaccines are needed. One approach to boost potency of BCG is to combine it with adjuvants. An adjuvant is a compound that can promote, modulate and improve vaccine immunogenicity. An adjuvant can also reduce required dosage of target antigen and modulate antigen-specific immune responses in a qualitative manner, such as Th1 and Th2 responses. Recent progress in innate immunity has shown that TLRs, RIG-I, and NLRs, specifically NOD2 recognize a variety of nucleic acid ligands that stimulate innate immune response and promote adjuvant-like activity.

Vertebrate systems are constantly under attack by invading microorganisms and have evolved immune-mediated defense for elimination of the pathogen. The mammalian immune system comprises of components of innate and acquired immunity. Innate immune system recognizes microorganisms via a limited number of germ-line encoded pathogen recognition receptors (PRRs) (3,4). Phagocytes such as macrophages and dendritic cells mediate the innate immune response. Acquired immune response is characterized by specificity that involves lymphocytes that carry antigen-specific receptors generated by mechanisms such as gene-rearrangement. Innate immunity plays an important role in regulating liver injury, fibrosis, and regeneration. For example, activation of natural killer cells (NK cells) by Interferons could be a novel strategy to treat liver fibrosis. This is because activation of NK cells can kill specifically activated hepatic stellate cells (HSCs) thereby ameliorating liver fibrosis and liver tumor formation. Hence the oligonucleotide analogs disclosed in this invention may have utility in inhibiting liver fibrosis, and progression of liver cancer.

Microbes have also evolved clever strategies to evade immune response that protect host cells from infection. Indeed, both DNA and RNA viruses inhibit cellular IFN production (type-I, IFN-α, IFN-β). Intracellular IFNs are potent antiviral cytokines whose expression/production is mediated by the transcription factor IRF3 (IFN regulatory factor 3) present in the cytoplasm of uninfected cells. IRF3 is activated once the cells are infected and viral components (also known as pathogen associated molecular patterns (PAMPS, e.g., viral genome, viral proteins etc) are recognized by specialized viral sensors or pattern recognition receptors (PRRs). Activated IRF3 translocates to the nucleus to transactivate IFN gene expression. IFN production induces protective antiviral effects (via paracrine and autocrine activity) through a variety of mechanisms such as, (i) activation of innate and adaptive immune responses, (ii) induction of antiviral state in cells by production of antiviral and beneficial pro-inflammatory factors, and (iii) controlled apoptosis of virus-infected cells. PRRs are therefore essential components of the IFN-response. Most recently, NOD2, a member of the family of nucleotide oligomerization domain (NOD) proteins, has been found to be a PRR which detects single-stranded RNA (ssRNA) viruses including RSV and influenza A. Interestingly, like the viral sensor RIG-I, activation of NOD2 also results in triggering the signaling cascade for IFN production and the induction of NF-κβ, which promotes a controlled pro-inflammatory response to potentiate the antiviral action of IFN. Since, NOD2 is a viral sensor that detects a broad range of ssRNA viruses such as RSV and Influenza A, it presents a unique host target for antiviral discovery and to combat antiviral resistance.

Similar to NOD2, RIG-I is a host cytosolic protein that recognizes double-stranded viral RNA as a PAMP that activates type1 Interferon immune defenses thereby inhibiting viral replication and also suppressing cellular permissiveness for virus infection (6-15). RIG-I is a viral sensor that detects a broad range of RNA viruses such as flaviviruses including Hepatitis C Virus, Sendai virus, Influenza virus, as well as, Vesicular stomatitis virus, Rabies virus and Japanese encephailitis virus, it presents a unique host target for broad-spectrum antiviral activity. It is noteworthy that although HBV is a DNA virus, it uses a pregenomic RNA template for the initiation of DNA synthesis and potentially therefore RIG-I may be a receptor for HBV pgRNA.

It has been discovered that certain dinucleotide compositions have potential for stimulation of innate immunity and induction of interferon production through activation of RIG-I pathway. Such compounds may also be useful prophylactically against viral infections and useful as adjuvants in vaccines.

The viral sensor RIG-I is a multimeric cytosolic protein consisting of a C-terminal regulatory domain (RD), two terminal caspase activation and recruitment domains (CARDS), as well as, a central ATPase domain. Viral double-stranded RNA (dsRNA) and 5'-triphosphate are two PAMPs that enable RIG-I to discriminate pathogenic RNA (dsRNA with and without triphosphate) from host RNA (which usually has a "Cap" modification at the end) (6-14). Furthermore, RIG-I has the ability to sense viral RNA through the phenomenon of translocation (Myong et al., Science 323, 1070. 2009). The RIG-I translocation and repetitive shuttling on dsRNA of the viral genome is the trigger for RIG-I to undergo conformational change, activate its ATPase, and expose CARDS for ubiquitination. In the next step, CARDS interacts with mitochondrial antiviral signaling (MAVS) [also known as interferon beta stimulator [(IPS-1), or VISA] to elicit downstream signaling that leads to type I IFN expression (IFN-α, β).

NOD2 and RIG-I are multimeric proteins, which are structurally and organizationally very similar. Thus, like RIG-I, NOD2 contains CARD domain. In addition, both RIG-I and NOD2 possess nucleotide-binding pockets located in NBD (nucleotide binding domains) (for NOD2) and helicase (for RIG-I) domains. Molecular modeling studies show that certain dinucleotide compositions have structural similarity to nucleoside triphosphate (NTP) structures that bind to NBD. We hypothesize that short oligonucleotides act as NTP mimics that bind to the NBD of NOD2 (and RIG-I) and cause their activation for downstream antiviral action.

The inventor(s) discovered that the nucleosides, short oligonucleotide compounds or analogs thereof of the invention can modulate immune pathways involving Toll-like receptors (TLRs), non-TLR receptors, such as, the Retinoic acid inducible gene-1 (RIG-I), and Nucleotide oligomerization proteins (NODs), collectively known as TLR, RLRs, and NLRs. Activation of these pathways by their respective ligands can induce the production of various cytokines, and chemokines, such as Interleukins, Interferons, NF-KB, TNF-alpha, etc, and also cause the induction of certain cellular proteins with antimicrobial activity thereby providing antimicrobial immunity. Conversely, the present inventor(s) designed compounds for causing inhibition of the inflammatory pathways, leading to beneficial effects in autoimmune diseases.

The present inventor(s) unexpectedly discovered that the nucleosides, short oligonucleotide compounds, and analogs thereof according to the invention can be used as adjuvants for vaccines. The compounds of the invention have therapeutic utility against a variety of infectious diseases caused by bacterial and viral agents. The compounds of the invention are also useful in treating or preventing autoimmune diseases, such as, allergy, asthma, inflammatory disorders, and other diseases, such as, cancer.

Therefore, the invention provides methods for treating or preventing various conditions, diseases, infections, or viruses that are delineated herein.

Definitions

In order that the invention may be more readily understood, certain terms are first defined and collected here for convenience.

Compounds of the invention comprise one or more modifications from "natural" nucleic acids, i.e., natural internucleosidic linkages, or nucleobases G, C, T, U, A etc. Modifications include, for example, modifications of the internucleotidic linkage, the base, or the sugar moiety.

A nucleoside unit is represented by the internationally accepted convention of line drawing. In the example below a 2'-substituted ribonucleoside is represented in both the conventional structure and the corresponding line drawing format

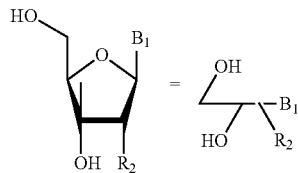

The sugar units attached to $B_1$ and $B_2$ that give rise to α or β N- or C-nucleoside includes, but not limited to, furanose, deoxyribofuranose, ribose, and arabinose.

The term "administration" or "administering" includes routes of introducing a compound(s) to a subject to perform their intended function. Examples of routes of administration that can be used include injection (subcutaneous, intravenous, parenterally, intraperitoneally, intrathecal), oral, inhalation, rectal and transdermal. The pharmaceutical preparations are, of course, given by forms suitable for each administration route. For example, these preparations are administered in tablets or capsule form, by injection, inhalation, topical by lotion or ointment; and rectal by suppositories. Oral administration is preferred. The injection can be bolus or can be continuous infusion. Depending on the route of administration, the compound can be coated with or disposed in a selected material to protect it from natural conditions which may detrimentally affect its ability to perform its intended function.

The compound can be administered alone, or in conjunction with either another agent as described above (e.g., a vaccine) or with a pharmaceutically-acceptable carrier, or both. The compound can be administered prior to the administration of the other agent, simultaneously with the agent, or after the administration of the agent. Furthermore, the compound can also be administered in a proform which is converted into its active metabolite, or more active metabolite in vivo.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the invention, any of the aryls, substituted aryls, heteroaryls and substituted heteroaryls described herein, can be any aromatic group. Aromatic groups can be substituted or unsubstituted.

The term "alkyl," as used herein, refer to saturated, straight- or branched-chain hydrocarbon radicals containing between one and six, or one and twelve carbon atoms, respectively. Examples of C1-C6 alkyl radicals include, but are not limited to, methyl, ethyl, propyl, isopropyl, n-butyl, tert-butyl, neopentyl and n-hexyl radicals; and examples of C1-C12 alkyl radicals include, but are not limited to, ethyl, propyl, isopropyl, n-hexyl, octyl, decyl, dodecyl radicals.

The terms "aralkyl" or "arylalkyl" embrace aryl-substituted alkyl radicals such as benzyl, diphenylmethyl, triphenylmethyl, phenylethyl, and diphenylethyl.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "cycloalkyl," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo[2.2.2]octyl.

The terms "substituted aryl", "substituted alkyl," "cycloalkyl", as used herein, refer to aryl, alkyl and cycloalkyl groups as previously defined, substituted by independent replacement of one, two, or three or more of the hydrogen atoms thereon with substituents including, but not limited to, —F, —Cl, —Br, —I, —OH, protected hydroxyl, —NO2, —CN, —NH2, protected amino, —NH—C1-C12-alkyl, —NH—C2-C12-alkenyl, —NH—C2-C12-alkenyl, —NH—C3-C12-cycloalkyl, —NH-aryl, —NH-heteroaryl, —NH-heterocycloalkyl, -dialkylamino, -diarylamino, -diheteroarylamino, —O—C1-C12-alkyl, —O—C2-C12-alkenyl, —O—C2-C12-alkenyl, —O—C3-C12-cycloalkyl, —O-aryl, —O—heteroaryl, —O-heterocycloalkyl, —C(O)—C1-C12-alkyl, —C(O)—C2-C12-alkenyl, —C(O)—C2-C12-alkenyl, —C(O)—C3-C12-cycloalkyl, —C(O)-aryl, —C(O)-heteroaryl, —C(O)-heterocycloalkyl, —CONH2, —CONH—C1-C12-alkyl, —CONH—C2-C12-alkenyl, —CONH—C2-C12-alkenyl, —CONH—C3-C12-cycloalkyl, —CONH-aryl, —CONH-heteroaryl, —CONH-heterocycloalkyl, —OCO2-C1-C12-alkyl, —OCO2-C2-C12-alkenyl, —OCO2-C2-C12-alkenyl, —OCO2-C3-C12-cycloalkyl, —OCO2-aryl, —OCO2-heteroaryl, —OCO2-heterocycloalkyl, —OCONH2, —OCONH—C1-C12-alkyl, —OCONH—C2-C12-alkenyl, —OCONH—C2-C12-alkenyl, —OCONH—C3-C12-cycloalkyl, —OCONH-aryl, —OCONH-heteroaryl, —OCONH-heterocycloalkyl, —NHC(O)—C1-C12-alkyl, —NHC(O)—C2-C12-alkenyl, —NHC(O)—C2-C12-alkenyl, —NHC(O)—C3-C12-cycloalkyl, —NHC(O)-aryl, —NHC(O)-heteroaryl, —NHC(O)-heterocycloalkyl, —NHCO2-C1-C12-alkyl, —NHCO2-C2-C12-alkenyl, —NHCO2-C2-C12-alkenyl, —NHCO2-C3-C12-cycloalkyl, —NHCO2-aryl, —NHCO2-heteroaryl, —NHCO2-heterocycloalkyl, —NHC(O)NH2, —NHC(O)NH—C1-C12-alkyl, —NHC(O)NH—C2-C12-alkenyl, —NHC(O)NH—C2-C12-alkenyl, —NHC(O)NH—C3-C12-cycloalkyl, —NHC(O)NH-aryl, —NHC(O)NH-heteroaryl, —NHC(O)NH-heterocycloalkyl, NHC(S)NH2, —NHC(S)NH—C1-C12-alkyl, —NHC(S)NH—C2-C12-alkenyl, —NHC(S)NH—C2-C12-alkenyl, —NHC(S)NH—C3-C12-cycloalkyl, —NHC(S)NH-aryl, —NHC(S)NH-heteroaryl, —NHC(S)NH— heterocycloalkyl, —NHC(NH)NH2, —NHC(NH)NH—C1-C12-alkyl, —NHC(NH)NH—C2-C12-alkenyl, —NHC(NH)NH—C2-C12-alkenyl, —NHC(NH)NH—C3-C12-cycloalkyl, —NHC(NH)NH-aryl, —NHC(NH)NH-heteroaryl, —NHC(NH)NH-heterocycloalkyl, —NHC(NH)—C1-C12-alkyl, —NHC(NH)—C2-C12-alkenyl, —NHC(NH)—C2-C12-alkenyl, —NHC(NH)—C3-C12-cycloalkyl, —NHC(NH)-aryl, —NHC(NH)-heteroaryl, —NHC(NH)-heterocycloalkyl, —C(NH)NH—C1-C12-alkyl, —C(NH)NH—C2-C12-alkenyl, —C(NH)NH—C2-C12-alkenyl, —C(NH)NH—C3-C12-cycloalkyl, —C(NH)NH-aryl, —C(NH)NH-heteroaryl, —C(NH)NH-heterocycloalkyl, —S(O)—C1-C12-alkyl, —S(O)—C2-C12-alkenyl, —S(O)—C2-C12-alkenyl, —S(O)—C3-C12-cycloalkyl, —S(O)-aryl, —S(O)-heteroaryl, —S(O)-heterocycloalkyl-SO2NH2, —SO2NH—C1-C12-alkyl, —SO2NH—C2-C12-alkenyl, —SO2NH—C2-C12-alkenyl, —SO2NH—C3-C12-cycloalkyl, —SO2NH-aryl, —SO2NH-heteroaryl, —SO2NH-heterocycloalkyl, —NHSO2-C1-C12-alkyl, —NHSO2-C2-C12-alkenyl, —NHSO2-C2-C12-alkenyl, —NHSO2-C3-C12-cycloalkyl, —NHSO2-aryl, —NHSO2-heteroaryl, —NHSO2-heterocycloalkyl, —CH2NH2, —CH2SO2CH3, -aryl, -arylalkyl, -heteroaryl, -heteroarylalkyl, -heterocycloalkyl, —C3-C12-cycloalkyl, polyalkoxyalkyl, polyalkoxy, -methoxymethoxy, -methoxyethoxy, —SH, —S—C1-C12-alkyl, —S—C2-C12-alkenyl, —S—C2-C12-alkenyl, —S—C3-C12-cycloalkyl, —S-aryl, —S-heteroaryl, —S-heterocycloalkyl, or methylthiomethyl. It is understood that the aryls, heteroaryls, alkyls, and the like can be further substituted.

The term "steroidal", as used herein, refers to any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins. Examples of steroidal structure includes, but not limited to, cholesterol, cholestanol, 3α-cyclo-5-α-cholestan-6-β-ol, cholic acid, cholesteryl formiate, cholestanyl formiate.

The term "modified nucleoside", as used herein, refers to any nucleoside that includes a modified heterocyclic base, a modified sugar moiety, or a combination thereof. In some embodiments, the modified nucleoside is a non-natural pyrimidine or purine nucleoside, as herein described. Examples of the modified nucleoside include, but not limited to, 2'-substituted ribonucleoside an arabinonucleoside or a 2'-deoxy-2'-flouroarabinoside, deaza-adenine, deaza-guanine.

For purposes of the invention, the term "short oligonucleotide(s)" refers to a mono, di or polynucleoside formed from 1 to about 6 linked nucleoside units. Such short nucleotides can be obtained from existing nucleic acid sources, including genomic or cDNA, but are preferably produced by synthetic methods. The nucleoside residues can be coupled to each other by any of the numerous known internucleoside linkages. Such internucleoside linkages may be modified or unmodified and include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "short nucleotide" also encompasses polynucleosides having one or more stereospecific internucleoside linkage (e.g., (RP)- or (SP)-phosphorothioate, alkylphosphonate, or phosphotriester linkages. The short nucleotides of the invention include any such internucleoside linkage, whether or not the linkage comprises a phosphate group. In certain preferred embodiments, these internucleoside linkages may be modified or unmodified and include without limitation, phosphodiester, phosphorothioate, or phosphorodithioate linkages, or combinations thereof.

The term "short nucleotide(s)" also encompasses additional substituents including, without limitation, protein groups, lipophilic groups, intercalating agents, diamines, folic acid, cholesterol and adamantane.

The term "short nucleotide(s)" also encompasses any other nucleobase containing polymers, including, without limitation, peptide nucleic acids (PNA), peptide nucleic acids with phosphate groups (PHONA), locked nucleic acids (LNA).

Examples of PNA and LNA are shown below:

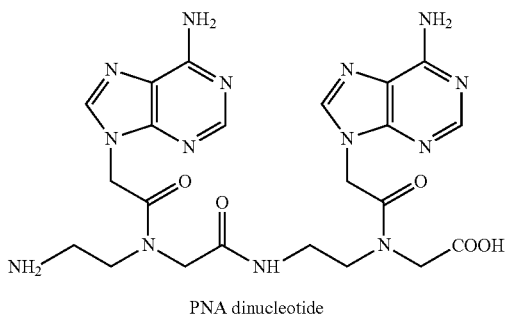

PNA dinucleotide

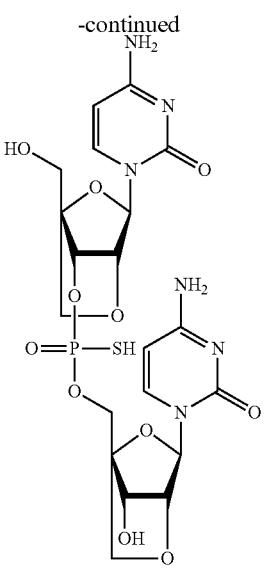

LNA dinucleotide

A "nucleotide" refers to a sub-unit of a nucleic acid (whether DNA or RNA or analogue thereof such as peptide nucleic acid (PNA) and locked nucleic acid (LNA)), which includes an internucleotide linkage, a sugar group and a heterocyclic base, as well as analogs of such sub-units. A "nucleoside" references a nucleic acid subunit including a sugar group and a heterocyclic nucleobase. It will be appreciated that, as used herein, the terms "nucleoside" and "nucleotide" will include those moieties which contain not only the naturally occurring internucleotide linkages (with respect to "nucleotides") such as phosphodiester internucleotide linkage; naturally occurring sugar moieties such as a ribose and deoxyribose moieties; and naturally occurring nucleobases such as purine and pyrimidine bases, e.g., adenine (A), thymine (T), cytosine (C), guanine (G), or uracil (U), but also modified internucleotide linkages, modified sugar moieties and modified purine and pyrimidine bases or analogs thereof or any combination of modified and unmodified internucleotide linkage, sugar moiety and purine and pyrimidine bases. Other examples of modified nucleosides include acyclonucleosides, which consists of ring-opened versions of the ribose and deoxyribose moieties. Correspondingly, such ring-opened nucleosides may be used in forming modified nucleotides. Other examples of modified nucleosides include C-nucleosides such as pseudo-isocytidine, and nucleoside mimics including nucleoside isosteres such as peptide nucleic acid monomers, and locked nucleic acid monomers.

Nucleobases include naturally occurring purine and pyrimidine nucleobases and modified nucleobases that include but are not limited to methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-methoxy guanine, 8-methoxy adenine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl) uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, 2,6-diaminopurine 5-trifluoromethyl thymine, 6-chloro-adenine, 7-deaza-adenine. Other examples without limitation include 5-fluoro-Uracil, 5-trifluoromethyl Thymine, 6-choro-Adenine, 2-cyclopentyloxy-Adenine, 7-deaza-Adenine.

In certain embodiments, the base B may be unnatural nucleobases including the universal nucleobases. Such examples of base B without limitation include difluorotolyl, nitropyrrolyl and nitro-imidazolyl and so on.

It should also be understood that a "modified base" also referred to as a "modified nucleobase", includes a nitrogen containing compound that may or may not be heterocyclic. Such preferred nitrogen containing compounds include but are not limited to —NHR18 wherein R18 is hydrogen, butyloxycarbonyl (Boc), benzyloxycarbonyl, allyl, substituted or unsubstituted alkyl, substituted or unsubstituted cycloalkyl, substituted or unsubstituted aralkyl, substituted or unsubstituted aryl, substituted or unsubstituted heteroaryl, or heterocyclic.

The term "modified nucleobase" is further intended to include heterocyclic compounds that are not nucleosidic bases in the most classical sense but that can serve as nucleosidic bases. Such compounds include "universal bases" as are known in the art. Universal bases may include an aromatic ring moiety, which may or may not contain nitrogen atoms. In some embodiments, a universal base may be covalently attached to the C-1' carbon of a pentose sugar of the nucleoside. Examples of universal bases include 3-methyl-propynylcarbostyryl (PIM), 3-methylisocarbostyryl (MICS), and 5-methyl isocarbostyryl moieties. Additional examples include Inosine derivatives, azole carboxamide analogues, nitroazoles, and nitroimidazoles.

Examples of modified nucleotide and nucleoside sugar moieties include but are not limited to: trehalose, arabinose, 2'-deoxy-2'-substituted pentose moiety, 2'-O-substituted pentose moiety, ribose, lyxose, and xylose, or hexose sugar group. For purposes of the invention, the term "2'-substituted" of any of the named sugar groups such as "2'-substituted ribonucleoside" or "2'-substituted arabinoside" includes ribonucleosides or arabinonucleoside in which the hydroxyl group at the 2'-position of the pentose moiety is substituted to produce a 2'-substituted or 2'-O-substituted ribonucleoside or arabinonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methyl ribonucleosides (also indicated herein as 2'-OMe) or 2'-O-methyl arabinosides and 2'-O-methoxyethyl ribonucleosides or 2'-O-methoxyethyl arabinosides. The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

Examples of modified internucleotide linkages include but are not limited to: substituted and unsubstituted phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages.

The compounds of the present invention contain one or more asymmetric centers and can thus occur as racemates and racemic mixtures, single enantiomers, diastereomeric mixtures and individual diastereomers. The present invention is meant to include short nucleotide compounds having the B-D stereochemical configuration for the five-membered furanose ring, that is, short nucleotide compounds in which the substituents at C-1 and C-4 of the five-membered furanose ring have the β-stereochemical configuration ("up" orientation which is typically denoted by a bold line in some formulas depicted herein).

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Certain prodrug moieties are, for example, propionoic acid esters and acyl esters. Prodrugs which are converted to active forms through other mechanisms in vivo are also included.

Abbreviations

Abbreviations, which may be used in the descriptions of the scheme and the examples that follow, are:
AcOH for acetic acid;
Boc$_2$O for di-tert-butyl-dicarbonate;
Boc for t-butoxycarbonyl;
Bpoc for 1-methyl-1-(4-biphenylyl)ethyl carbonyl;
Bz for benzoyl;
Bn for benzyl;
BocNHOH for tert-butyl N-hydroxycarbamate;
t-BuOK for potassium tert-butoxide;
Bu$_3$SnH for tributyltin hydride;
CDI for carbonyldiimidazole;
CH$_2$Cl$_2$ for dichloromethane;
CH$_3$ for methyl;
CH$_3$CN for acetonitrile;

DMSO for dimethyl sulfoxide;
EtOAc for ethyl acetate;
EtOH for ethanol;
Et$_2$O for diethyl ether;
HCl for hydrogen chloride;
MeOH for methanol;
MOM for methoxymethyl;
Ms for mesyl or —SO$_2$—CH$_3$;
Ms$_2$O for methanesulfonic anhydride or mesyl-anhydride;
NaCl for sodium chloride;
NaH for sodium hydride;
NaHCO$_3$ for sodium bicarbonate or sodium hydrogen carbonate;
Na$_2$CO$_3$ sodium carbonate;
NaOH for sodium hydroxide;
Na$_2$SO$_4$ for sodium sulfate;
NaHSO$_3$ for sodium bisulfite or sodium hydrogen sulfite;
Na$_2$S$_2$O$_3$ for sodium thiosulfate;
NH$_2$NH$_2$ for hydrazine;
NH$_4$HCO$_3$ for ammonium bicarbonate;
NH$_4$Cl for ammonium chloride;
OH for hydroxyl;
OMe for methoxy
OEt for ethoxy
TEA or Et$_3$N for triethylamine;
TFA trifluoroacetic acid;
THF for tetrahydrofuran;
TPP or PPh$_3$ for triphenylphosphine;
Ts for tosyl or —SO$_2$—C$_6$H$_4$CH$_3$;
Ts$_2$O for tolylsulfonic anhydride or tosyl-anhydride;
TsOH for p-tolylsulfonic acid;
Ph for phenyl;
TBS for tert-butyl dimethylsilyl;
TMS for trimethylsilyl;
TMSCl for trimethylsilyl chloride.

Compounds of the Invention

The invention provides nucleosides, short oligonucleotide compounds, or analogs thereof, or pharmaceutically acceptable salts, racemates, enantiomers, diastereomers, geometric isomers, or tautomers thereof. The invention also includes the compounds in their prodrug and metabolite forms.

In certain embodiments, the invention provides di-, and tri-nucleotides including, but not limited to, 3-dApsU$_{2'-OMe}$, 3'dApsA$_{7deaza}$, and 3'-dApsTpsC and their analogs where "ps" refers to phosphorothioate internucleotidic linkages.

The compounds of the invention include, such as, the compounds of formula (I):

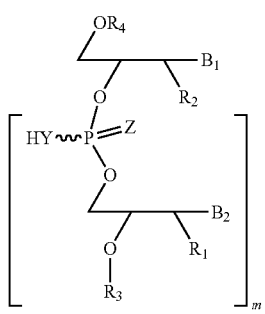

or pharmaceutically acceptable salts, racemates, enantiomers, diastereomers, geometric isomers, or tautomers thereof, wherein:

R$_1$ and R$_2$ are each independently, H, OH, O-akyl, alkyl, substituted alkyl, cycloalkyl, aryl, substituted aryl, aralkyl, heterocyclic, O-aryl, O-heteroarylaryl, or heterocyclic;

R$_3$ is selected from hydrogen, alkyl, substituted alkyl, C(O)-alkyl, C(O)O-alkyl, C(O)-aryl, C(O)O-aryl, C(O)NH-alkyl, and C(O)NH-aryl;

Y and Z are each independently, O or S;

B$_1$ and B$_2$ are each independently adenine, guanine, thymine, cytosine, uracil or modified nucleosides;

m=1 to 6;

R$_4$ is independently H, alkyl, substituted alkyl, C(O)-alkyl, C(O)O-alkyl, C(O)-aryl, C(O)O-aryl, C(O)NH-alkyl, and C(O)NH-aryl a monophosphate, diphosphate, or triphosphate group.

In one embodiment, the compounds of the invention include a compound of formula (II):

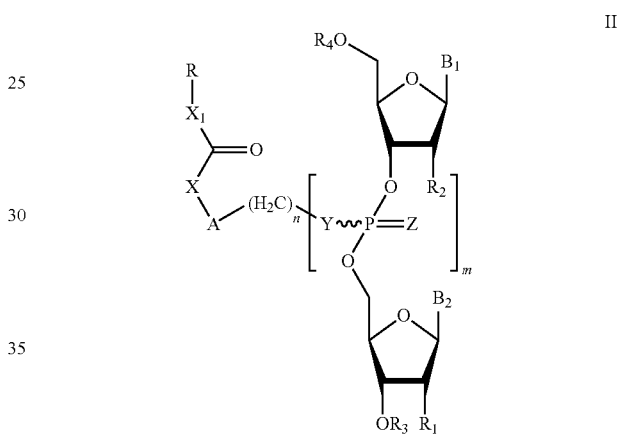

or a pharmaceutically acceptable salt, racemate, enantiomer, diastereomer, geometric isomer, or tautomer thereof, wherein:

X=absent, O, NH, NR, or S;

X$_1$=absent, O, or NH;

A=absent, aryl, or aralkyl;

n=0, 1, 2, 3, 4, or 5;

R=alkyl, substituted alkyl, cycloalkyl, aryl, substituted aryl, aralkyl, heterocylic, O-alkyl, O-heteroaryl, or steroidal;

R$_1$ and R$_2$ are each independently, H, OH, O-akyl, alkyl, substituted alkyl, cycloalkyl, aryl, substituted aryl, aralkyl, heterocyclic, O-aryl, O-heteroarylaryl, or heterocyclic;

R$_3$ is selected from hydrogen, alkyl, substituted alkyl, C(O)-alkyl, C(O)O-alkyl, C(O)-aryl, C(O)O-aryl, C(O)NH-alkyl, and C(O)NH-aryl;

Y and Z are each independently, O or S;

B$_1$ and B$_2$ are each independently adenine, guanine, thymine, cytosine, uracil or modified nucleosides;

m=1 to 6;

R₄ is independently H, alkyl, substituted alkyl, C(O)-alkyl, C(O)O-alkyl, C(O)-aryl, C(O)O-aryl, C(O)NH-alkyl, and C(O)NH-aryl a monophosphate, diphosphate, or triphosphate group.

In one embodiment, the compound of the invention is a compound of the following structure:

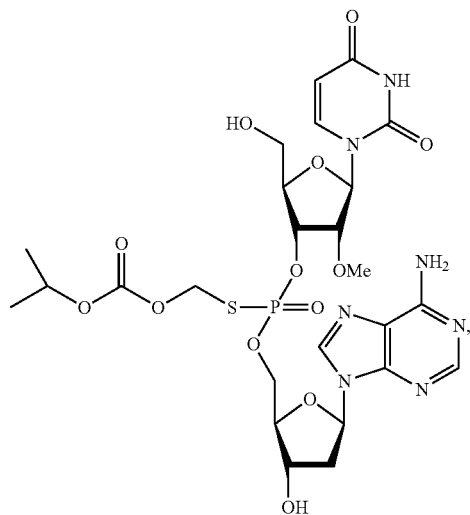

or a pharmaceutically acceptable salt, racemate, enantiomer, diastereomer, geometric isomer, or tautomer thereof.

In another embodiment, the compound of the invention is a compound of the following structure:

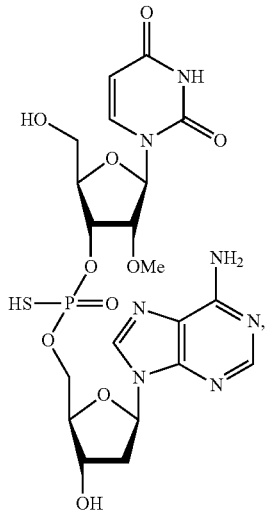

or a pharmaceutically acceptable salt, racemate, enantiomer, diastereomer, geometric isomer, or tautomer thereof.

Other embodiments of the invention provide the following compounds or pharmaceutically acceptable salts, racemates, enantiomers, diastereomers, geometric isomers, or tautomers thereof:

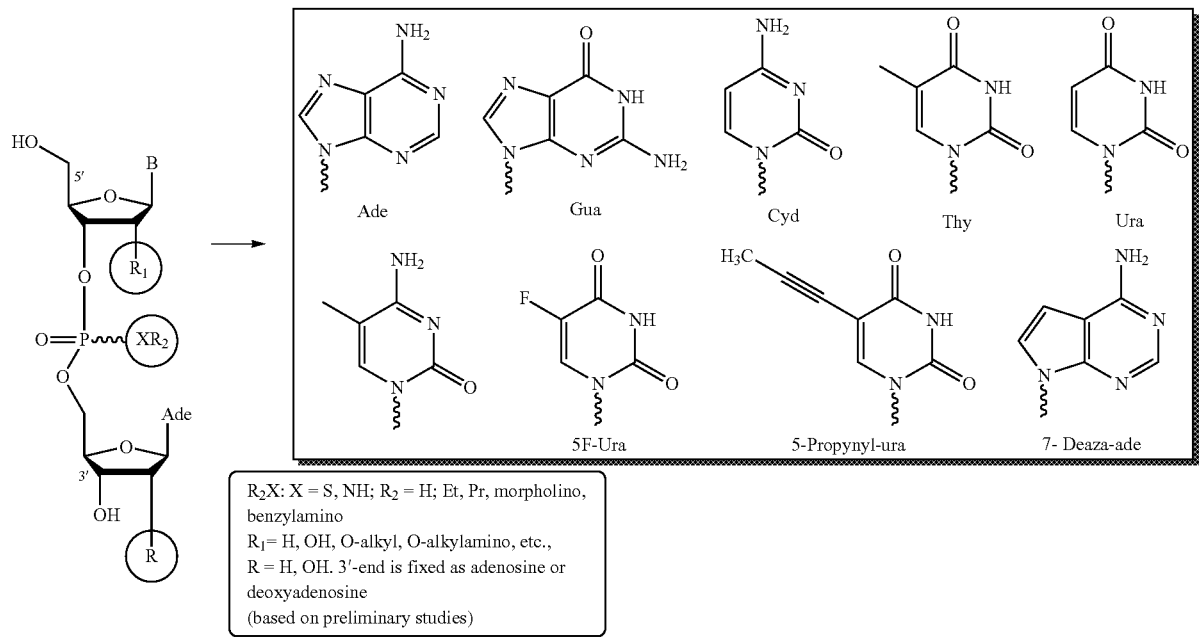

SB 44; R = H; R₁ = OMe; B = Ure; XR₂ = OCH₂—O—COO-ipr.
SB 40; XR₂ = SH; R₁ = OMe; B = Ure
All compounds wil be synthesized using standad
phosphoramidite, or H-phosphonate chemistry similar to preliminary studies Further, the compounds of the invention may comprise one or more modifications from "natural" nucleic acids, i.e., natural internucleosidic linkages, or nucleobases G, C, T, U, A etc. Modifications include, for example, modifications of the internucleotidic linkage, the base, or the sugar moiety.

The invention also provides tautomers, stereoisomers, optical isomers, N-oxides, hydrates, solvates, polymorphs, pharmaceutically acceptable esters, amides, salts, prodrugs, and isotopic derivatives of the compounds delineated herein.

The structures of some of the compounds of the invention include asymmetric carbon atoms. Accordingly, the isomers arising from such asymmetry (e.g., all enantiomers and diastereomers) are included within the scope of this invention, unless indicated otherwise. Such isomers can be obtained in substantially pure form by classical separation techniques and/or by stereochemically controlled synthesis.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques.

Methods of obtaining a compound of the invention include purchasing, synthesizing or otherwise acquiring the compound. Synthesizing compounds of the invention is within the means of chemists of ordinary skill in the art; exemplary methods for preparing compounds of the invention are described herein. Methods for optimizing reaction conditions, if necessary minimizing competing by-products, are known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds.

Methods and Uses

The compounds of the invention are useful in a broad range of therapeutic areas that involve host immune components including but not limited to: allergy, inflammation, autoimmune diseases, COPD, asthma and so on. By virtue of the fact that these compounds can act as modulators of immune response through a number of mechanisms, they have therapeutic uses in autoimmune diseases. For example, since the compounds have the potential to stimulate innate immune response, they can be utilized either alone or in combination with other agents in the treatment of a variety of cancers including but not limited to melanoma, myeloma, carcinoma, glioblastoma and sarcoma. For example, since certain oligonucleotide compositions have the potential to inhibit immune response, they can be utilized either alone or in combination with other agents in the treatment of a variety of autoimmune diseases including, but not limited to, allergy, asthma, COPD and multiple sclerosis.

Since many interferon-associated gene products are capable of inducing apoptosis, the compounds may induce selective cell death of cancer cells. Hence compositions of the invention may be used either alone or in combination or sequentially with a vaccine or another or other agent(s).

The invention thus provides a method of treating a microbial infection in a subject (or host) by administering to the subject (or host) identified as in need thereof an effective amount of a compound of the invention.

In another aspect, the invention provides a method of improving an immune system response in a subject against a disease, condition, infection, or virus. The method comprises administering to the subject an effective amount of a compound of the invention as a vaccine adjuvant.

The invention also provides a method for the prevention and treatment of a viral infection in a host (or subject), including human, by administering an effective amount of a compound of the invention. The compound of the invention can be administered alone or in combination or sequentially with a vaccine or other agents.

In still another aspect, the invention provides a method for the prevention and treatment of a bacterial infection in a host (or subject), including human, by administering an effective amount of a compound of the invention. The compound of the invention can be administered alone or in combination or sequentially with a vaccine or other agents.

Further, the invention provides a method of the prevention and treatment of a parasitic infection in a host (or subject), including human, by administering an effective amount of a compound of the invention. The compound of the invention can be administered alone or in combination or sequentially with a vaccine or other agents.

A method for the prevention and treatment of a fungal infection in a host (or subject), including human, is also disclosed. The method includes administering an effective amount compound of the invention, which can be administered alone or in combination or sequentially with a vaccine or another or other agent(s).

In certain embodiments of the methods, the compound of the invention is a short oligonucleotide compound or analog thereof of formula (I), or a pharmaceutically acceptable salt, racemate, enantiomer, diastereomer, geometric isomer, or tautomer thereof.

In other embodiments, the compound of the invention is a short oligonucleotide compound or analog thereof of formula (II), or a pharmaceutically acceptable salt, racemate, enantiomer, diastereomer, geometric isomer, or tautomer thereof.

In one embodiment, the compound of the invention is

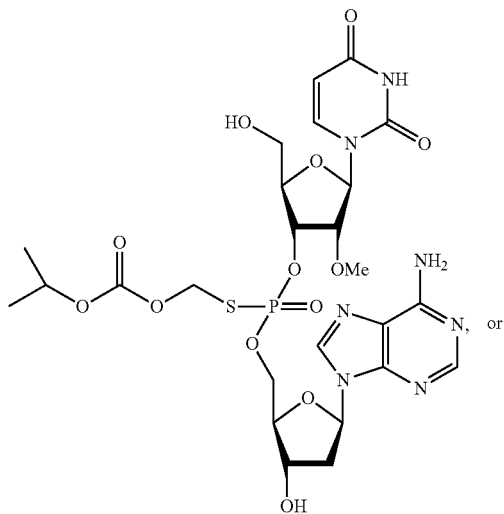

-continued

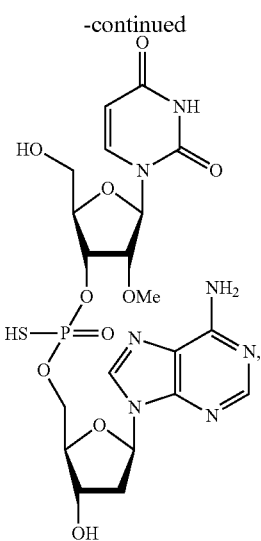

or a pharmaceutically acceptable salt, racemate, enantiomer, diastereomer, geometric isomer, or tautomer thereof.

Further, the invention provides the use of the compounds provided in the following chart, or pharmaceutically acceptable salts, racemates, enantiomers, diastereomers, geometric isomers, or tautomers thereof:

In another embodiment, the methods of the invention are used against a virus.

In a further embodiment, the methods are used for treating or preventing a cancer.

The methods of the invention comprise administering to the subject a therapeutically effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

Another aspect of the present invention comprises in treating with a compound of the present invention in combination with one or more agents useful for treating a disease. For example, such agents active against viruses include, Lamivudine (3TC), Adefovir, Tenofovir, Gancyclovir, acyclovir, Interferon, Ribavirin, Telbivudine; other agents against COPD, asthma, allergy allergic rhinitis include, but are not limited to Theophylline, Alvesco (Ciclesonide), Patanase (Olapatidine hydrochloride) Litairis (Ambresentan)(Gilead) Xyzal (Levocetirizine dihydrochloride), Brovana (Arformoterol tartrate), Spiriva (Tritropium bromide) Clarinex, Declomethsone dipropionate, Remodunil (treprostenil), Xopenex, Duoneb (albuterol and Tritropium bromide), Formeterol fumarate, Tracleer (bosantan), Triamcinolone acetonide, Budesonide, Singulair, Serevent, Tilade

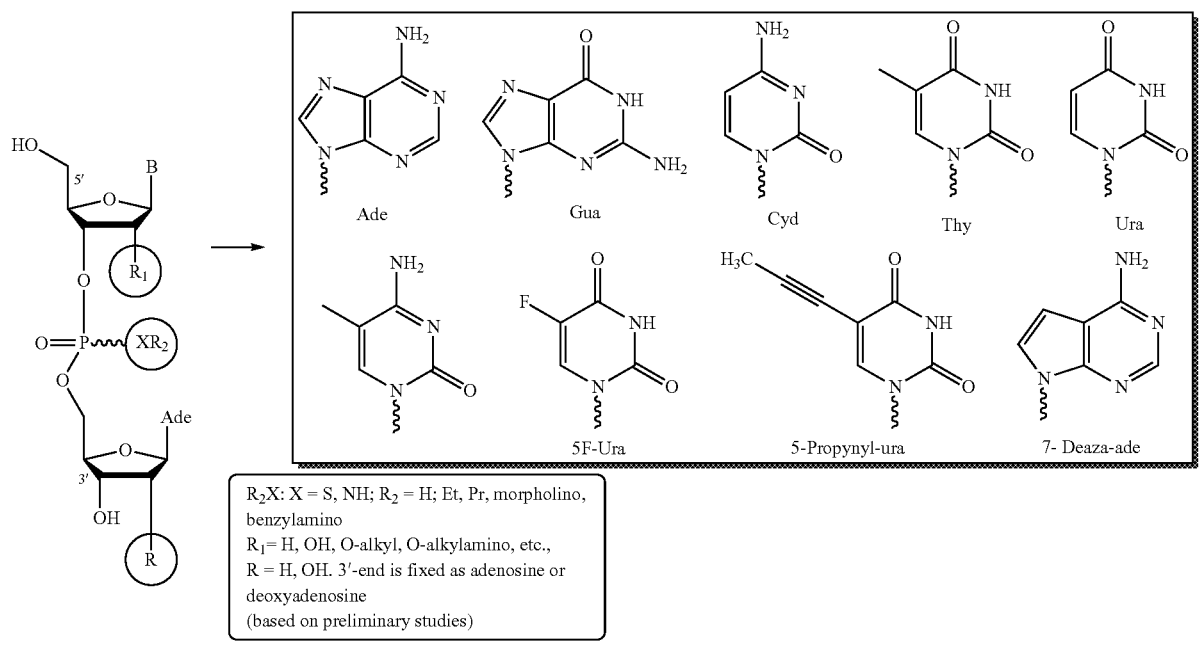

SB 44; R = H; R$_1$ = OMe; B = Ure; XR$_2$ = OCH$_2$—O—COO-ipr.
SB 40; XR$_2$ = SH; R$_1$ = OMe; B = Ure
All compounds wil be synthesized using standad
phosphoramidite, or H-phosphonate chemistry similar to preliminary studies According to the methods of the invention, a compound of the invention can be administered alone, or together with a vaccine (such as, a BCG vaccine) or one or more additional agents.

In one embodiment, a compound of the invention and the vaccine are administered for treating or preventing a microbial infection.

(inhaler and nebulizer), Zyflo, Accolate, Cedax, Zyrtec, herceptin. Among anticancer agents for example but not limited to taxol, paclitaxel, cisplatin, Herceptin, Gleevac, Interferon and so on.

In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents includes in principle any combination with any pharmaceutical composition for treating viral, bacterial, parasitic, fungal infections and so on. When a compound of the present invention or a pharmaceutically acceptable salt thereof is, used in combination with a second therapeutic agent, the dose of each compound may be either the same as or different from the dose when the compound is used alone.

It will be understood that the scope of combinations of the compounds of this invention with other agents includes in principle any combination with any pharmaceutical composition for treating COPD, asthma, allergic rhinitis, cancer and so on. When a compound of the present invention or a pharmaceutically acceptable salt thereof is, used in combination with a second therapeutic agent, the dose of each compound may be either the same as or different from the dose when the compound is used alone.

For the purposes of this invention, antimicrobial is meant to denote compounds that are effective against viral, bacterial, fungal and parasitic infections.

The term "therapeutically effective amount" of a compound of the invention, as used herein, mean a sufficient amount of the compound so as to produce a beneficial biological response in a biological sample or in a subject. As well understood in the medical arts, a therapeutically effective amount of a compound of this invention will be at a reasonable benefit/risk ratio applicable to any medical treatment.

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, brain and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms. It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions

The invention provides pharmaceutical compositions comprising the compounds of the invention, and derivatives thereof in association with a pharmaceutically acceptable carrier. Another example of the invention is a pharmaceutical composition made by combining any of the compounds described above and a pharmaceutically acceptable carrier.

The pharmaceutical compositions of the present invention comprise at least one compound of the invention as an active ingredient or a pharmaceutically acceptable salt thereof, and may also contain a pharmaceutically acceptable carrier and excipients and optionally other therapeutic ingredients. By "pharmaceutically acceptable" is meant that the carrier, diluent, or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin.

When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Various stabilizers may be added that would stabilize the active pharmaceutical ingredient against degradation, such as amino acids or polyamines Other excipients could include without limitation PEG 400, glycine, Vitamin E derivatives, Sorbitan mono-oleate, Chitosan, Choline citrate, Sorbitan monostearate, Tween 80, Igepal CA 630, Brij 35, NP-40 and their analogous derivatives.

Compounds of the invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous reparation of sterile injectable solutions or dispersions. In all cases, the form is preferably sterile and is preferably fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with a therapeutically effective dosage of a compound of the present invention. The terms "administration of" and "administering a" compound should be understood to mean providing a compound of the invention to the individual in need. The routes of administration include for example without limitation oral, sublingual, transmucosal, intravenous, subcutaneous, intranasal, topical, vaginal, etc.

Regardless of the route of administration selected, the compound(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic to the patient. An exemplary dose range is from about 0.1 μg to 20 milligram per kilogram of body weight per day (mg/kg/day) (e.g., 0.1 μg/kg to 2 mg/kg, 0.3-3 μg/kg, 0.18-0.54 mg/kg). In other embodiments, the amount varies from about 0.1 mg/kg/day to about 100 mg/kg/day. In still other embodiments, the amount varies from about 0.001 μg to about 100 μg/kg (e.g., of body weight). Ranges intermediate to the above-recited values are also intended to be part of the invention.

The total daily inhibitory dose of the compounds of this invention administered to a subject in single, multiple or in divided doses can be in amounts, for example, from 0.01 to 50 mg/kg body weight or more usually from 0.1 to 25 mg/kg body weight.

Single dose compositions may contain such amounts or submultiples thereof to make up the daily dose. Multiple doses may be single doses taken at different time intervals. In general, treatment regimens according to the present invention comprise administration to a patient in need of such treatment from about 10 mg to about 1000 mg of the compound(s) of this invention per day in single or multiple doses.

Further, the compounds of the invention can be administered by multiple delivery routes such as oral, intravenous, sublingual, intranasal, topical and so on.

Kits

The invention provides kits for the treatment or prevention of a disease, condition or disorder delineated herein. In one embodiment, the kit includes a therapeutic or prophylactic composition containing an effective amount of a compound of the invention in unit dosage form. In some embodiments, a compound of the invention is provided in combination with a vaccine or a conventional therapeutic agent. In other embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, a compound of the invention is provided together with instructions for administering the compound to a subject having or at risk of a specific disease, condition or disorder delineated herein. The instructions will generally include information about the use of the composition for the treatment or prevention of the disease, condition, disorder, infection or virus. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Synthesis of Compounds

The focused library of nucleotide analogs described as illustrative examples in this invention was synthesized as before (17-22). Both solid-phase synthesis and solution phase strategies were used in a complimentary fashion to prepare the focused libraries as illustrated. The methods can be used for the synthesis of libraries with modifications at the sugar nucleobase and internucleotidic linkages. Several technology innovations in our laboratory facilitated the synthesis of nucleotide libraries: a) we have previously developed strategies for the synthesis of dinucleotide libraries using solid-phase phosphoramidite and H-phosphonate technologies (17-22). Recent technology innovations from our laboratory were also used for the solid-phase synthesis of dinucleotide compounds and analogs (17-22). (i) Ultra-fast preparation of amino-, and carboxy-functionalized solid-supports using microwave-assisted methods (ii) Novel methods for the loading of nucleosides on solid supports. An improved process for the large-scale preparation of nucleoside-loaded support was developed that involves the use of dimethylformamide (DMF) as a solvent. High nucleoside loadings of 80 to 300 micromol/g of support are obtained. (iii) A novel reactor called LOTUS® for loading of solid supports and solid-phase synthesis that facilitates large-scale synthesis of dinucleotides. LOTUS® is a multi-purpose reactor equipped with pneumatic valves for controlled delivery of reactants (20-22)

Example 1

The Rp,Sp mixture of the phosphorothioate analog 3-dApsU2'-OMe (1), was synthesized in large scale (1 millimol of nucleoside-loaded controlled-pore glass (CPG) support) using solid-phase phosphoramidite chemistry, (Beaucage, S. L.; Iyer, R. P. Tetrahedron 1993, 49, 1925) in conjunction with a specially fabricated LOTUS Reactor® (Padmanabhan, S.; Coughlin, J. E.; Iyer, R. P. Tetrahedron Lett. 2005, 46, 343; Iyer, R. P.; Coughlin, J. E.; Padmanabhan, S. Org. Prep. Proc. Intl. 2005, 37, 205). The dA-linked CPG support was prepared using our recently discovered ultrafast functionalization and loading process for solid supports. For the sulfurization of the internucleotidic dinucleoside phosphite coupled product, a solution of 3H-1, 2-benzodithiole-3-one-1,1,-dioxide (0.4 M in dry CH3CN) was employed (Iyer, R. P.; Regan, J. B.; Egan, W.; Beaucage, S. L. J. Am. Chem. Soc. 1990, 112, 1253).

Following processing, chromatographic purification, and lyophilization, the sodium salt of Rp,Sp 5 (~60:40 mixture) was obtained >96% pure, which was characterized by $^{31}$P and $^1$H NMR. Thus, solid-phase synthesis of focused library of dinucleotide compounds and analogs was readily performed. In a complementary strategy, solution-phase synthesis was also used for the synthesis of 1. These methodologies enabled the synthesis of compounds with a variety of chemical modifications.

Example 2

Synthesis of Compound 3

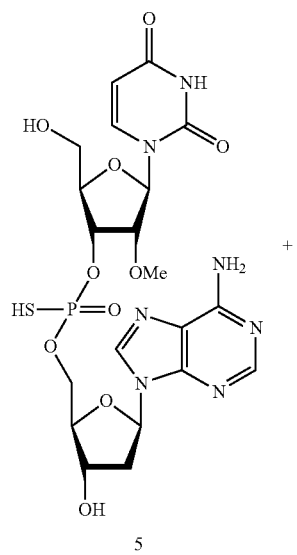

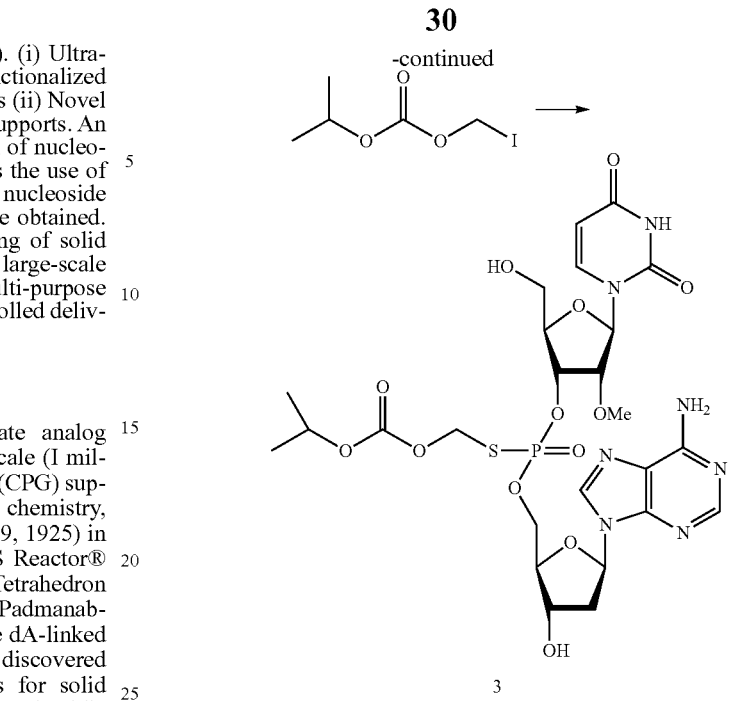

The target compound 3 was prepared in two steps.

Step 1. Preparation of Iodomethylisopropyl Carbonate: To a solution of anhydrous sodium iodide (6 g, 40 mmol) in anhy. acetonitrile (20 mL) chloromethyl isopropyl carbonate (2.9 g, 19 mmol) in anhydrous. acetonitrile (10 mL) was added drop wise over 20 min. The reaction mixture, covered with aluminum foil (protected from light) was stirred at room temperature overnight. The solid separated was filtered, washed with acetonitrile and the filtrate was concentrated under reduced pressure. Residue was dissolved in water (10 mL) and organics were extracted in ether (25 mL). Ether extracts were washed with sodium bisulfite (5%, 10 mL), later brine (10 mL). Organic layer was dried over anhydrous. sodium sulfate, filtered, concentrated and dried under high dried vacuum. Yield 2.72 g (58%); $^1$H-NMR δ 1.3 (d, 6H), 4.95 (m, 1H), 5.95 (s, 2H).

Step 2. Alkylation of Compound 5: To a solution of dinucleotide 1 (60 mg, 0.098 mmol) in water (HPLC, 400 mL) under stifling a solution of iodomethyl isopropyl carbonate (80 mg, 0.0166 mmol, 3.33 eq) in acetone (1 mL) was added. Additional acetone (1 mL) was added to get a clear solution to avoid any separation of oily globules of alkylating agent. The reaction mixture, covered in aluminum foil, was stirred for 3 h, concentrated under rotavap conditions and later in high vacuum to obtain the reaction mixture as a white solid. This was purified by silica column chromatography using initially chloroform and slowly with chloroform containing 2% to finally 8% methanol. The fractions, containing major component, were combined, concentrated and dried under high vacuum overnight. The desired pure product 3 was isolated in almost quantitative yield (68 mg); $^{31}$P-NMR (MeOH-d$_4$) δ 27.7, 28.6.

Figure 2:
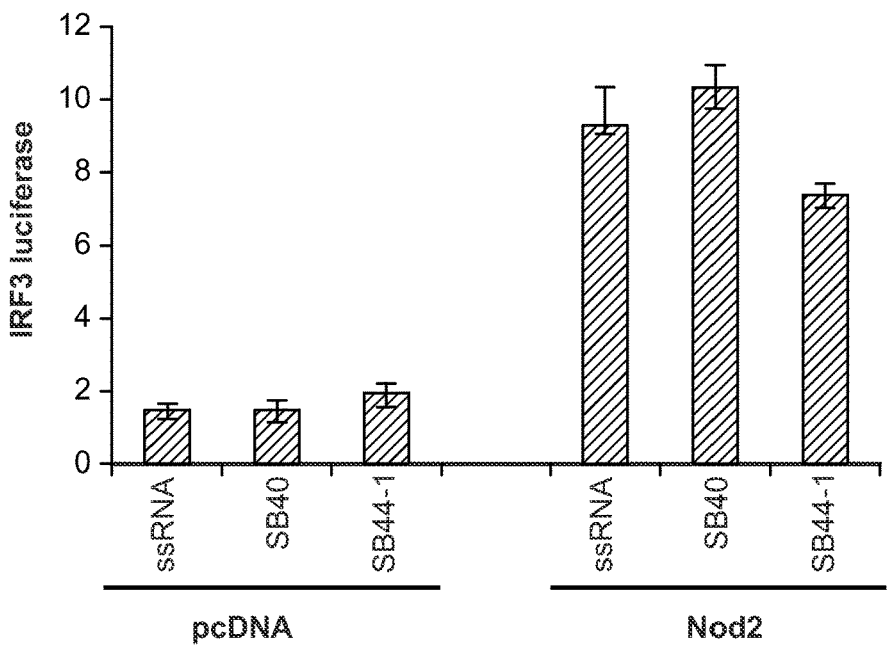
FIG. 2 demonstrates that IRF3 activation by SMNH compounds (SB 40 and SB 1B [SB 44-1]) is mediated via NOD2 activation.

Example 3
Discovery and Activity of SB 40, SB 44, and SB 1B as NOD2/RIG-I Ligands The evaluation of SMNH compounds for NOD2 activation was conducted by primary, secondary, and tertiary assays. In the primary assays, SMNH compounds were tested for the induction of IRF3 expression in HLE A549 cells, which are known to endogenously express NOD2. As shown in FIGS. 1-2, the dinucleotide analogs SB 40, SB 43, SB 44, and SB 1B but not related analogs such as the dinucleotides SB 50, SB 110, and SB 60, induced IRF3 activation. SB 44, a mixture of two isomers Rp and Sp, is a prodrug of SB 40. SB 1B—the Rp isomer of SB 44 and is shown as SB 44-1 in the FIGS. 1-2.

IRF3-luciferase transfected cells were incubated with either DMSO only (UT) or SMNH compounds (µM). Following 12 h incubation, luciferase activity was measured using Dual-Luciferase Reporter Assay System (Promega) according to the manufacturer's protocol. Transfection efficiency was normalized by measuring the expression of renilla Luciferase. Luciferase units (i.e., fold induction) were measured by standard methodology (mean±standard deviation; 3 independent experiments). The results are depicted in FIG. 1.

HEK 293 cells were transfected with NOD2, pcDNA and IRF3-luciferase. The cells were then incubated with ssRNA (0.5 mg/ml) or SMNH compounds (1 µM). Following 12 h incubation, Luciferase activity was measured as described previously. The luciferase assay results are presented as mean±S.D. from three independent experiments (detailed materials and methods employed in these assays, see: ref (28). The results are depicted in FIG. 2.

Figure 3:
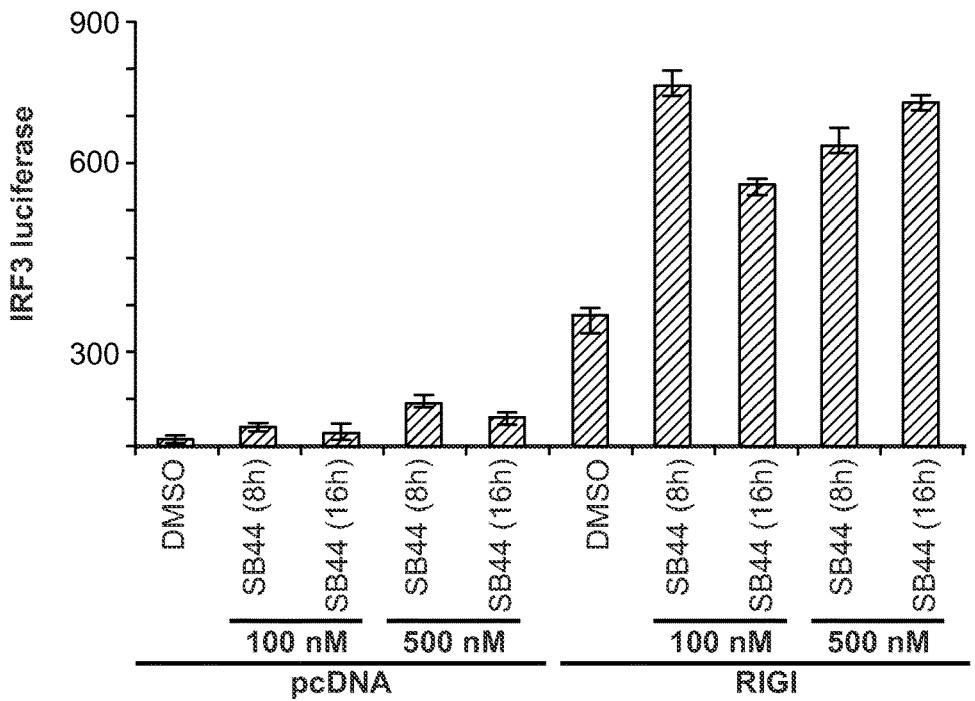
FIG. 3 shows IRF3 induction following activation of RIG-I in HLE cells by SB 44.

FIG. 3 shows that RIG-I activation by SB 44. HEK 293 cells were transfected with RIGI, pcDNA and IRF3-luciferase. The cells were then incubated with SB 44 (100 or 500 nM). Following 8 h or 16 h incubation, Luciferase activity was measured as described previously. The Luciferase assay results are presented as mean±S.D. from three independent experiments.

Figure 4:
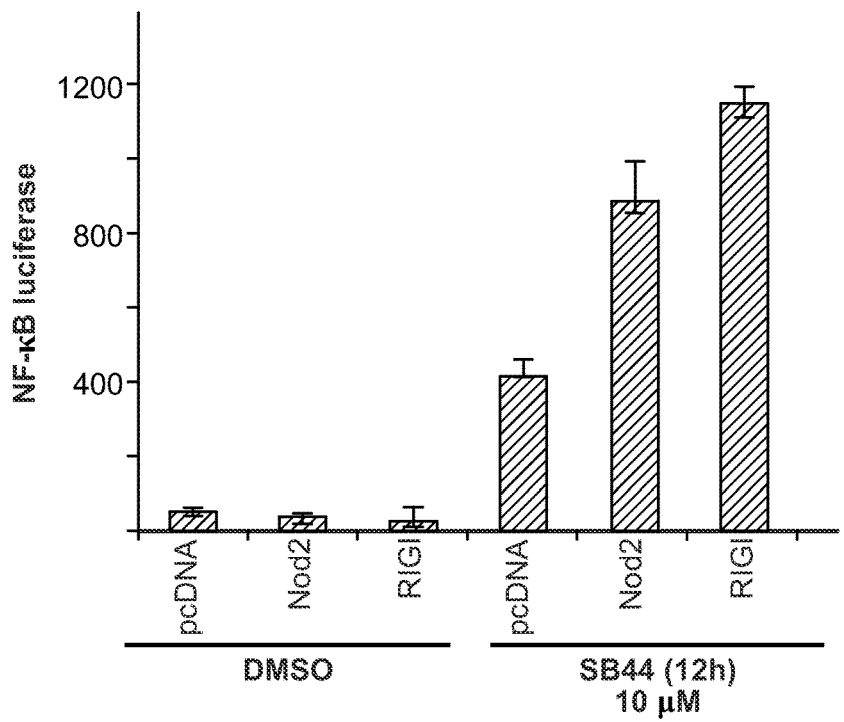
FIG. 4 demonstrates the induction of the transcription factor, NF-KB following activation of RIG-I and NOD2 by SB 44.

FIG. 4 demonstrates induction of NF-kB activity by SB 44 via RIGI and Nod2 activation. HEK 293 cells were transfected with RIGI, pcDNA, Nod2 and NF-kB-luciferase. The cells were then incubated with SB 44 (10 µM). Following 12 h incubation, Luciferase activity was measured as described previously. The Luciferase assay results are presented as mean±S.D. from three independent experiments.

FIG. 5 shows detection of activated IRF3 (phosphorylated IRF3 or phospho-IRF3) in SB 44-treated human lung epithelial cell (HLEC). Human lung epithelial A549 cells were incubated with either DMSO or SB 44 (500 nM). At indicated post-treatment time-points, the cell lysate was subjected to Western blotting with antibody specific for phosphorylated IRF3 (phospho-IRF3) (Cell signaling).

FIG. 6 shows detection of activated IRF3 (phosphorylated IRF3 or phospho-IRF3) in SB 44-treated human lung epithelial cell (HLEC). Human lung epithelial A549 cells were incubated with either DMSO or SB 44 (500 nM). At indicated post-treatment time-points, the cell lysate was subjected to Western blotting with antibody specific for phosphorylated IRF3 (phospho-IRF3) (Cell signaling).

Figure 9:
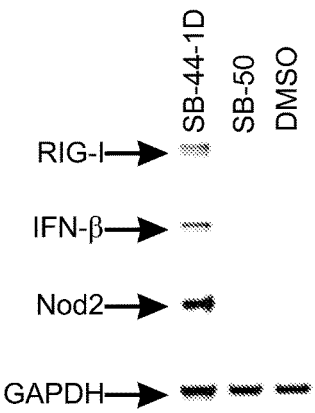
FIG. 9 shows the induction of responder genes RIG-I and NOD2 by SB 1B (shown as "SB-44-1-D"); SB 50 does not activate NOD2 and is used as a negative control.
Figure 10A:
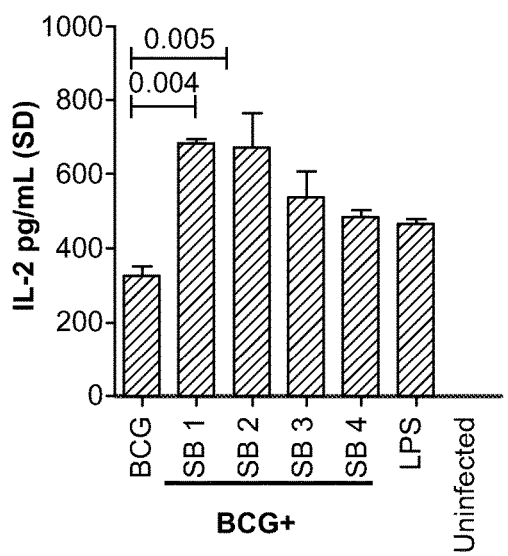
FIG. 10 (a-d) shows that SMNH compounds enhance in vitro presentation of peptide antigen-85B in macrophages which correlates with increased MHC-II expression (SB 44 shown as SB 1A).
Figure 10B:
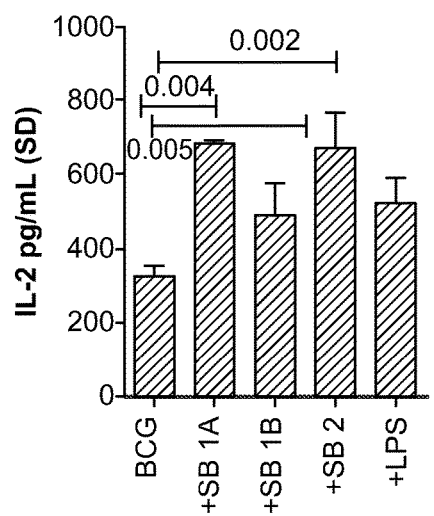
Figure 10C:
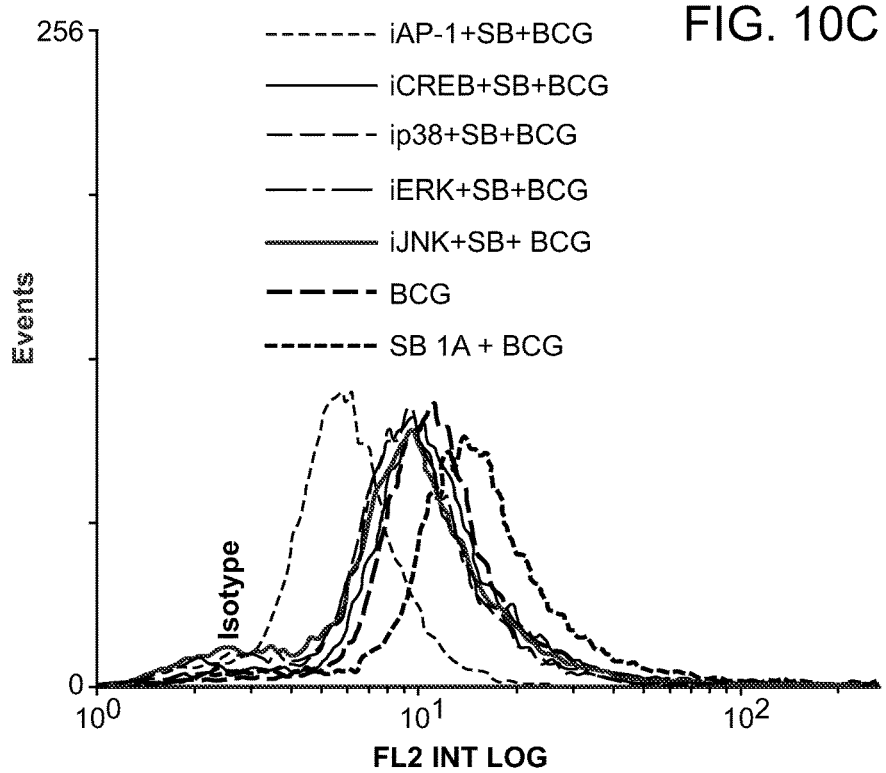
Figure 10D:
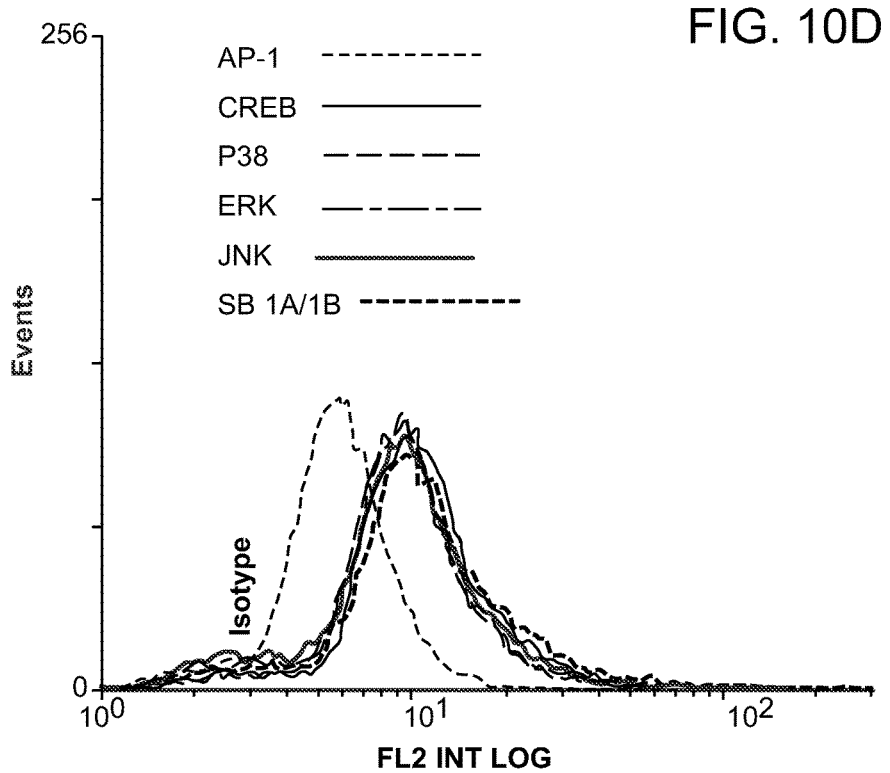
Figure 11A:
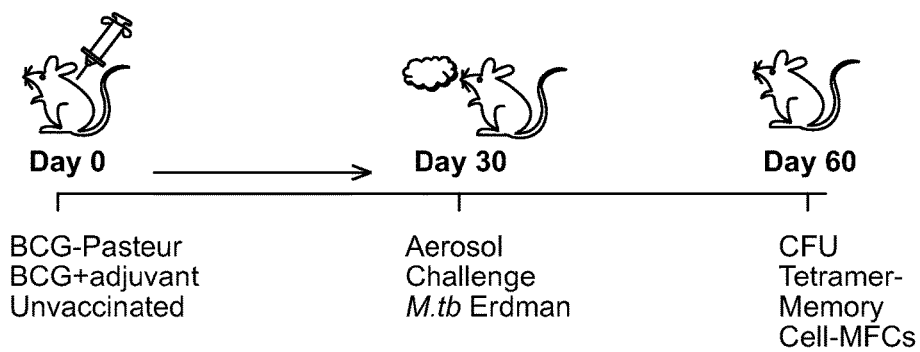
FIG. 11 (a-e): a) shows a model of the vaccine experiments in mice; b-e) are graphs showing that NOD2-activating compounds SB 1A (also as SB 44) and SB 1B are better than muramyl dipeptide (MDP) as adjuvants to boost efficacy of BCG vaccine against tuberculosis in mice.
Figure 11B:
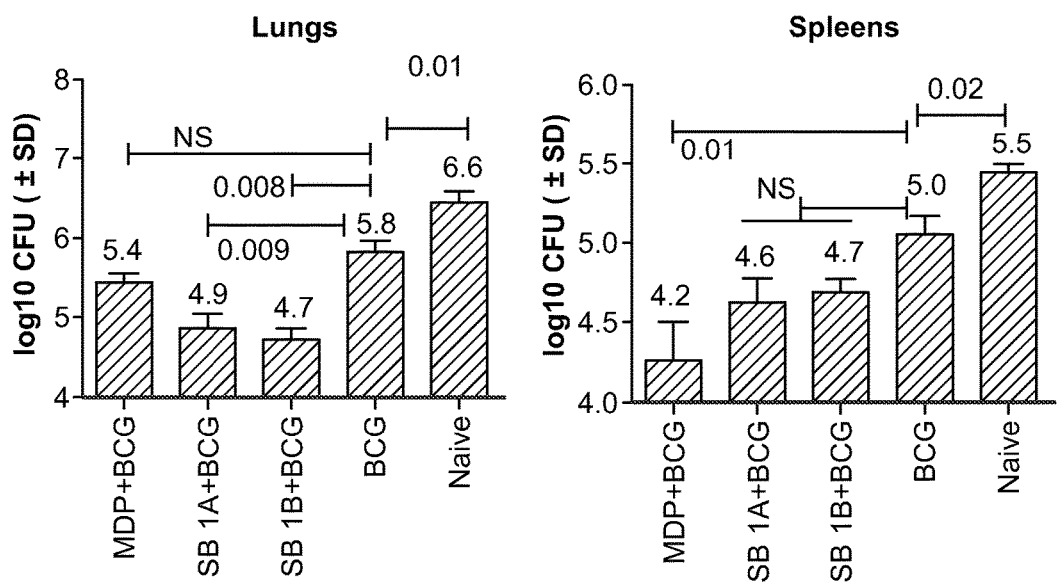
Figures 1, 12A:
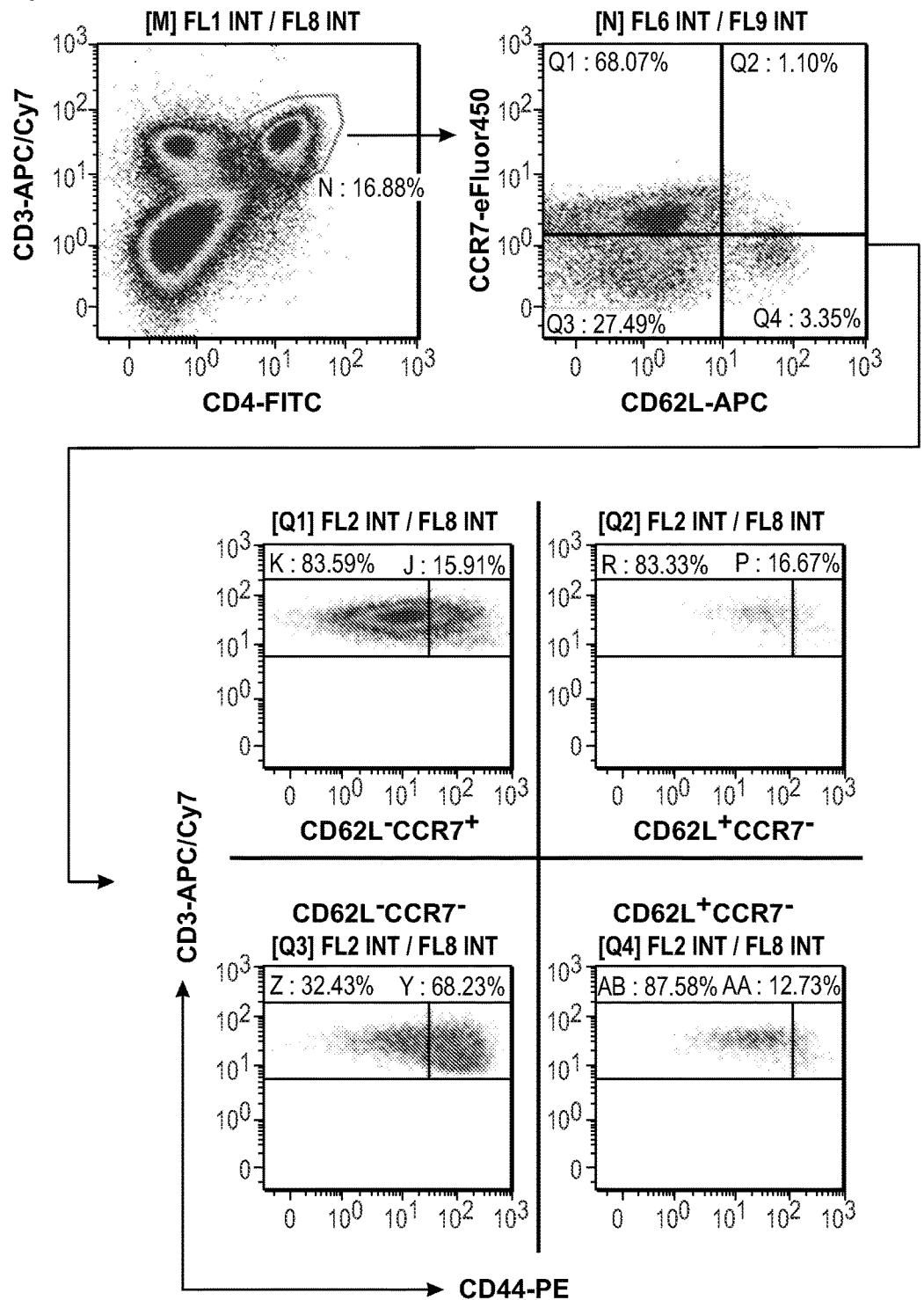
Figures 2, 12A:
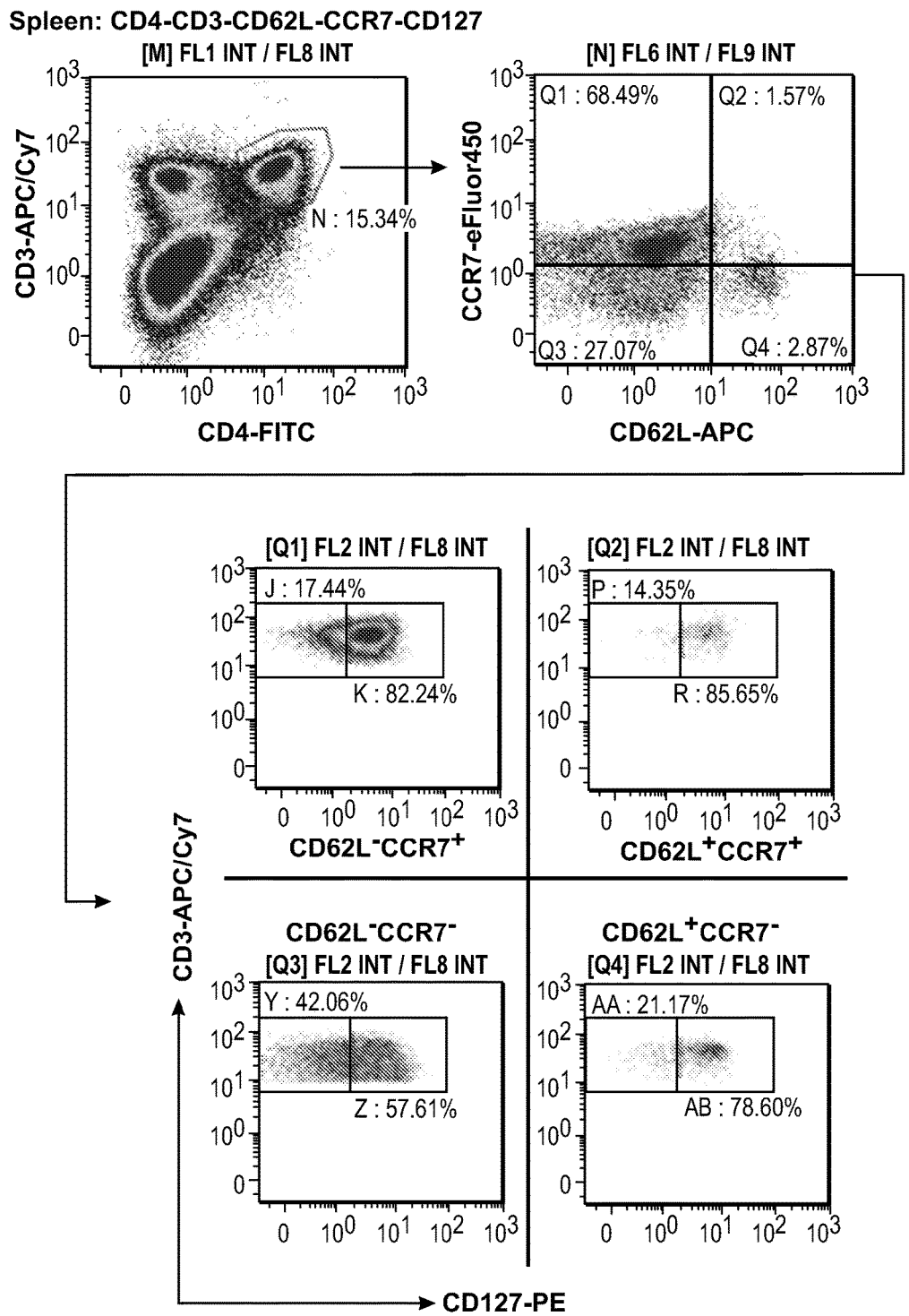
Figures 1, 12B:
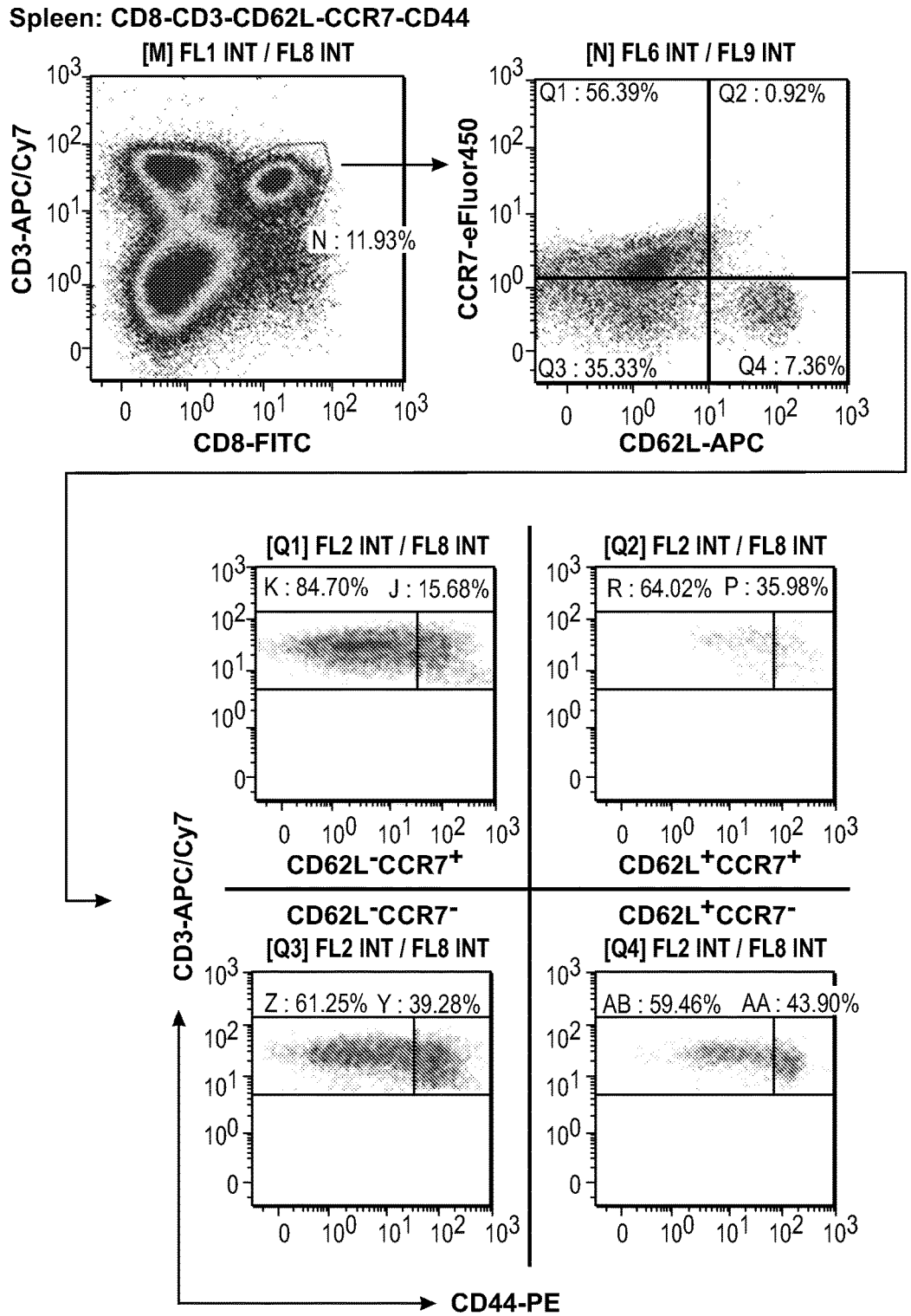
Figures 2, 12B:
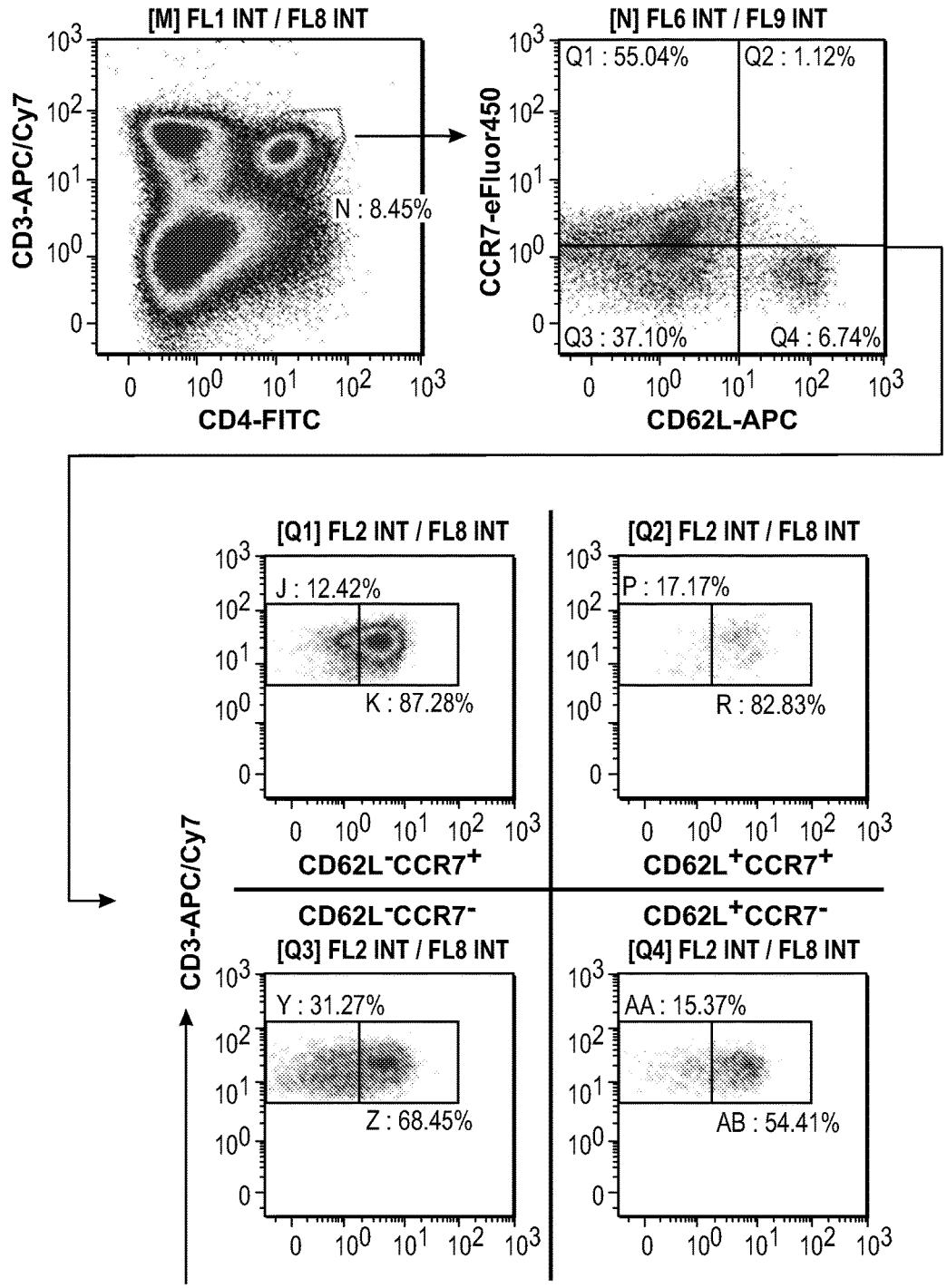
Figure 13:
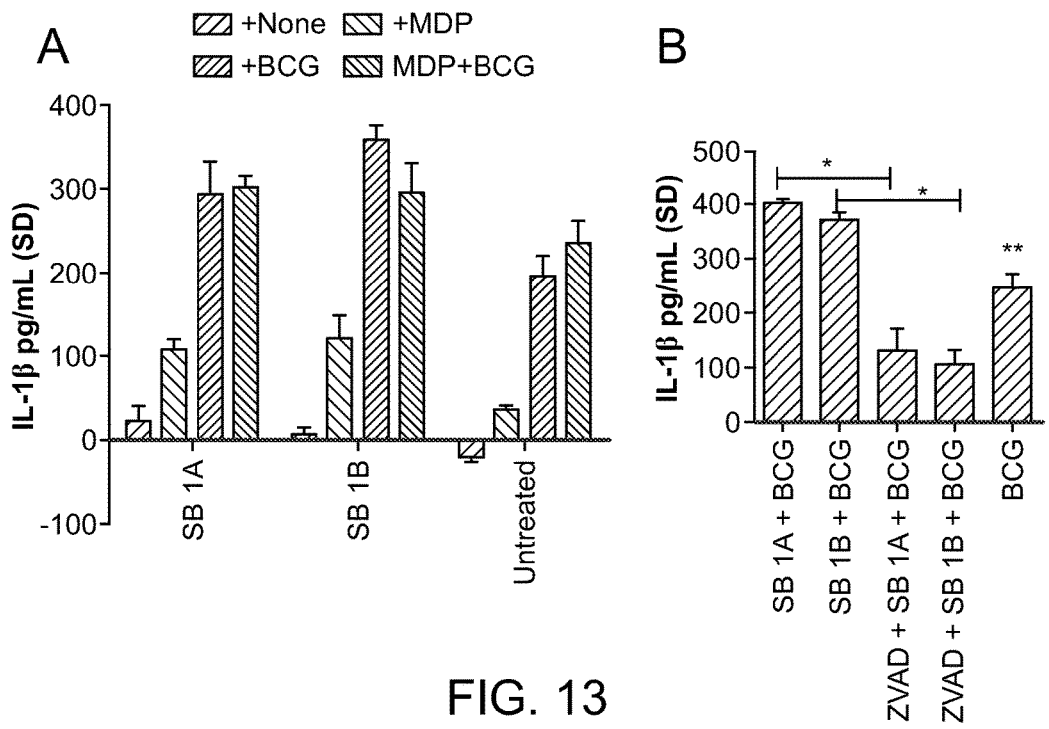
FIG. 13 (a-b) shows that NOD2-activating SB 1A (also as SB 44) and SB 1B (the Rp-isomer of SB 44) in combination with BCG vaccine induce protection against re-challenge of tuberculosis in mice, suggesting long-term protection.
Figure 14:
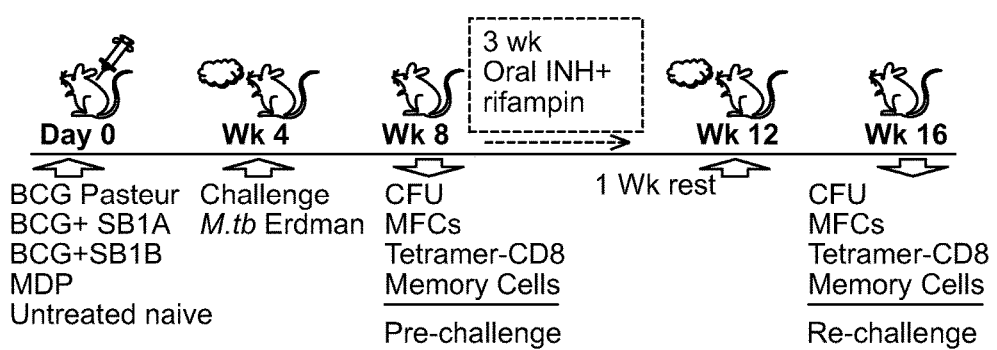
FIG. 14 shows a model developed to verify that SB 1A (also as SB 44) and SB 1B (the Rp-isomer of SB 44) induced MPECs can render long term protection by regenerating as strong effector T cells in mice.
Figure 16A:
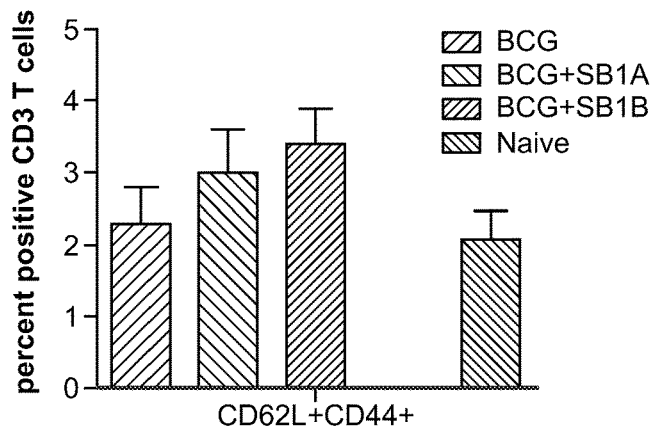
FIG. 16 shows that NOD2-activating SB 1A (also as SB 44) and SB 1B (the Rp-isomer of SB 44) compounds in combination with BCG vaccine induces a robust expansion of antigen specific CD8 T cells in the lungs of tuberculosis re-challenged mice.
Figure 16B:
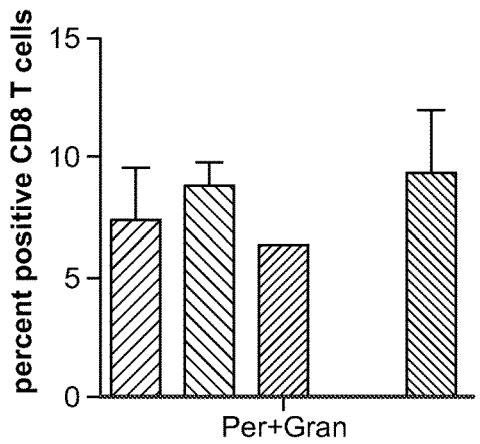
Figure 16C:
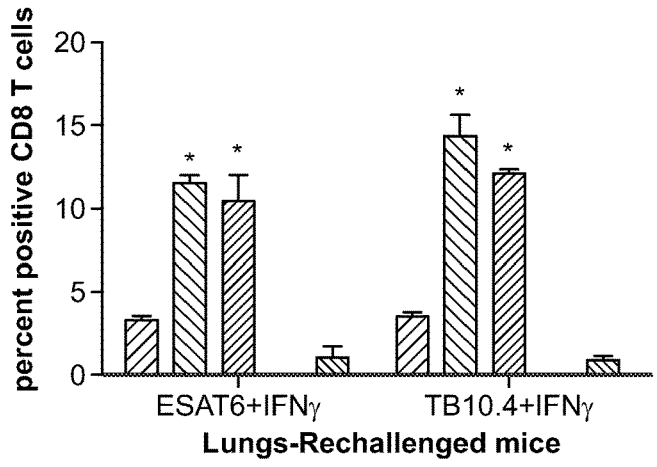

Further test results are depicted in FIGS. 7-9.

Conclusion and Discussions: Based on the above results, the compounds SB 40, SB 44 and SB 1B were evaluated for adjuvant-like activity in combination with BCG vaccine. The dinucleotide compounds SB 40, SB 44 and SB 1B, which activated NOD2/RIG-I, were also found to enhance antigen presentation in vitro, increase MHC-II in MΦs and cause dramatic increase in anti-TB T cell function of mice when used along with BCG. As mentioned before, SB 44 is a mixture of two isomers (Rp, and Sp) of which SB 1B is the Rp-isomer constituting ca. 55-60% in the mixture.

Example 4

Design of Optimal Ligands for NOD2 and RIG-I

For the discovery of optimal ligands for NOD2 and RIG-I, the dinucleotide structures SB 40 and SB 44 are employed as the initial leads for the synthesis of additional compounds involving both base and sugar modifications as shown below as illustrative examples. Both solid-, and solution phase synthetic strategies in conjunction with phosphoramidite, and H-phosphonate chemistries are employed for their synthesis. Many building blocks are commercially available or will be synthesized in-house.

Representative examples of compounds related to SB 40 and SB 44 are shown below:

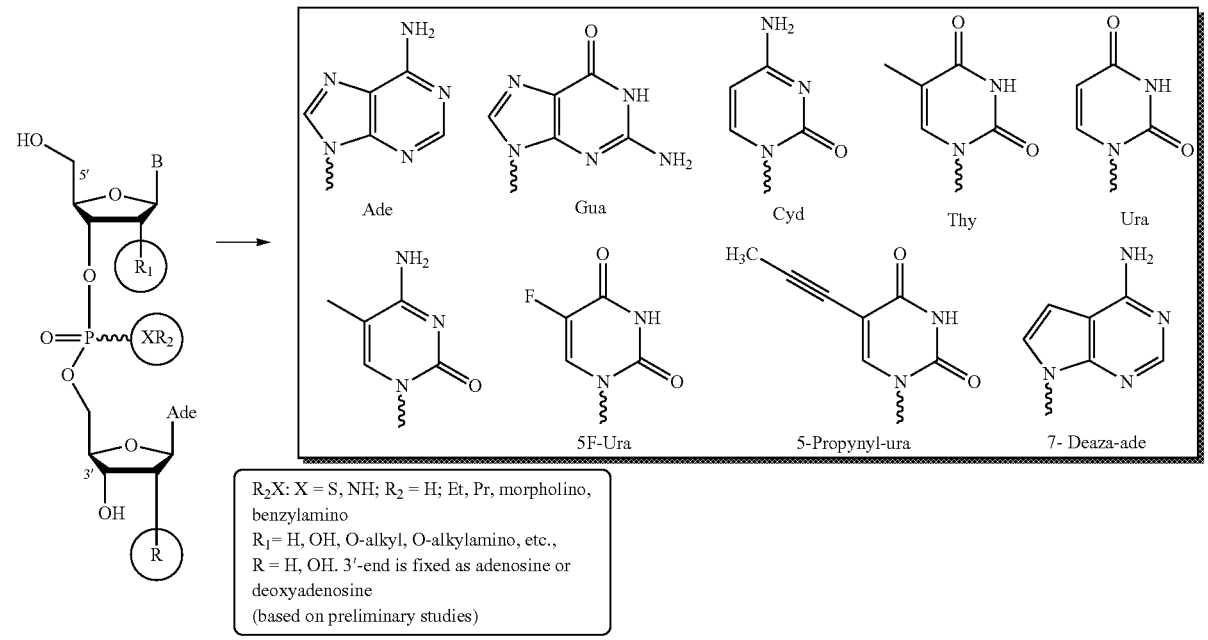

SB 44; R = H; $R_1$ = OMe; B = Ure; $XR_2$ = $OCH_2$—O—COO-ipr.
SB 40; $XR_2$ = SH; $R_1$ = OMe; B = Ure
All compounds wil be synthesized using standad
phosphoramidite, or H-phosphonate chemistry similar to preliminary studies

Example 5

Studies of NLR Ligands as Adjuvants with BCG Vaccine Using Macrophages and Mice Rationale for Adjuvant Development of SB 1B: Adjuvants are known to enhance the cytokine secretion in MΦs but their effects on the ability of MΦs and DCs to present antigens to activate T cells are unknown. Likewise, whether T cell function can be modulated for long term efficacy is also not clear. BCG is the most widely used vaccine in the world today used to prevent tuberculosis. It protects children against tuberculosis but has limited efficacy against adult TB perhaps because of a lack of long term efficacy. In this section we demonstrate that SB 1A and SB 1B enhanced MΦ function when infected with BCG vaccine, and they boost the activity of BCG both as a primary vaccine when given to mice, and as a booster vaccine with a potential to protect against reinfection with tuberculosis.

C57Bl/6 mouse bone marrow derived macrophages (MΦs) were treated with 10 μg/well of SMNH compounds 1-4 and LPS positive control (1 μg/mL) for 4 hours followed by infection with *Mycobacterium bovis Bacillus* Calmette Guerin (BCG) bacteria for 4 hours. BB7 T cells specific for Antigen-85B epitope were overlaid and supernatants collected after 18 hours were tested for IL-2 using sandwich ELISA (p values, t test).

FIG. 10 (*a-d*) show: a) Initial screening of most active SB compounds evaluated SB 1 (NOD2 agonist) and SB 3 and SB 44 (dinucleotides related to SB 1) along with LPS, a known TLR4 agonist. a) SB 1 and 2 enhance antigen presentation; b) SB 1A (SB 44) and SB 1B (SB 1B, the Rp-isomer of SB 44) were compared with SB 2 and LPS. The Rp-isomer of SB 44 (SB 1B) retain full activity; c) MΦs were treated with 5 μM each of inhibitors of signaling molecules (AP-1, CREB, and MAPKs (p38, ERK1/2 and JNK) for 2 hour followed by activation for 2 hours with the SB compounds and infection with BCG for 2 hours. MΦs were fixed and analyzed for surface MHC-II using flow cytometry. SB 1A enhances surface expression of MHC-II which is inhibited by blockade of either MAPKs or AP-1/CREB (>0.5 log 10 shift compared to SB 1A combination with BCG). SB 1B had similar activity (not shown); d) Inhibitors of MAPK or AP1/CREB have no effect on their own on MHC-II.

Example 6

NOD2-RIG-I Activating SB 1A and 1B Compounds Enhance the Efficacy of BCG Vaccine Against Experimental Aerosol-Induced Tuberculosis The Vaccine Experimental Design in Mice: C57Bl/6 mice were vaccinated with BCG alone or BCG mixed with SB 1A, SB 1B and MDP; this was followed 4 weeks later by aerosol challenge with *M. tuberculosis*. Mice were sacrificed 4 weeks later for the evaluation of protection (reduction in CFU counts of Mtb). Phenotype and function of T cells of spleens or lungs were measured using flow cytometry. FIG. 11(*a*)

FIG. 11(*b*) shows that SB 1A and SB 1B are potent adjuvants reducing Mtb counts of lungs better than either BCG or MDP+BCG (p values by 2-way ANOVA). Numbers above bars indicate log 10 bacterial load (MDP vs. SB 1A/SB 1B+BCG; p<0.02). SB 1A and SB 1B is also better than BCG vaccine in reducing Mtb counts of spleens. SB 1B enhances the numbers of multi-functional T cells compared to BCG vaccine but both SB 1A and SB 1B induce comparable levels of tetramer specific CD8 T cells (FIG. 11 (*c-d*)).

SB 1A induces better memory precursor T cells (MPECs) than BCG vaccine (FIG. 11*e*). Histogram illustrated below shows the flow cytometric analysis of T cell populations expressing memory markers in spleens.

C57Bl/6 mouse bone marrow derived primary macrophages were treated with SB 1A or SB 1B alone, MDP alone or in combination as indicated for 4 hrs. BCG was used for infection for 4 hrs and supernatants collected 18 hr later titrated for mature IL1β using ELISA. Macrophages were first treated with ZVAD-fmk (2 hrs) for caspase blockade followed by activation with SB 1A and SB 1B (4 hrs) and BCG infection (4 hrs). Cytokine was measured 18 hrs later. The results are presented in FIG. 12, showing that NOD2-activating compounds SB 1A and SB 1B induce IL-1β only in combination with either MDP or intact BCG bacilli through a caspase-dependent mechanism in macrophages.

NOD2-activating SB1A/1B combination with BCG vaccine induces protection against re-challenge of tuberculosis in mice suggesting long term protection. BCG vaccine is the only approved vaccine used to prevent TB, although it is weakly protective against aerosol induced TB in mice and induces poor central memory (29). This is believed to be due to inability of BCG to induce MPECs. It was found that SB compounds induced elevated MPECs (see FIG. 11(*e*)). MPECs which give rise to central memory are however present in low numbers in mice and their function can only be ascertained by their strong recall expansion into effector CD8 T cells.

Thus a new model was developed to verify that SB 1A and SB 1B induced MPECs can render long term protection by regenerating as strong effector T cells in mice. The model is shown in FIG. 14 where after a primary vaccination and challenge, Mtb as well as, vaccine are cleared through drug therapy allowing MPECs to rest. Then, the mice are re-challenged with virulent Mtb for evaluation of protection.

C57Bl/6 mice were vaccinated and challenged and were cleared of vaccine and Mtb organisms using isoniazid and rifampin for 3 weeks followed by resting and re-challenge with an aerosol dose of virulent Mtb. Four weeks later protection was evaluated through CFU counts of lungs and spleens and T cell analysis from 3 separate mice per group. Most importantly, SB 1B (SB 1B) combination with BCG protects twice as better than BCG both after primary and secondary rechallenge (p values by 2-way ANOVA; 5 mice per group per time point).

FIG. 15(*a-b*) shows that SB 1A or SB 1B combination with BCG vaccine retain the ability to mount a better recall response against re-challenge with tuberculosis.

Lungs of mice shown in FIG. 11 after re-challenge (week 16) were analyzed for CD8 T cells using flow cytometry. Histogram example shows the tetramer stain for CD8 T cells. Tetramer+IFNγ stains were used to measure functional T cells and tetramers+ CD44 stains were used to measure memory CD8 T cells against tuberculosis in the lungs. (FIG. 16 *a-b*)

Data show that lungs of vaccinated mice contain comparable numbers of CD62L+CD44+ central memory T cells and functional CD8 T cells that express perforin+granzyme. (FIG. 16 *c-d*) However, lungs contain elevated levels of Tetramer+IFNγ CD8 T cells which also express the memory markers CD62L and CD44. This suggests that SB 1A and SB 1B boost the magnitude of antigen specific memory T cells which are critical for longer-term containment of tuberculosis.

In summary, three separate studies with mice have already shown that SMNH combination with BCG vaccine enhances protection against both a primary challenge and secondary challenge with tuberculosis.

Example 7

Preclinical Studies of SB 44

A number of preclinical studies have been conducted using SB 44 and SB 40 and these studies are illustrative of outcomes with the lead adjuvant candidate SB 1B.

As illustrated by the studies using BCG, the mechanism of action of SB 44 and SB 40 involves the induction and activation of RIG-I and NOD2 in the presence of "foreign" nucleic acid. Most foreign nucleic acids have a signature pattern (PAMP, Pathogen-associated molecular pattern) in their structure that forms the basis of the selective recognition of these nucleic acids as "foreign" by RIG-I and NOD2. To illustrate this unique selectivity in the mechanism of action, several in vitro studies were carried out and are summarized below:

1). SB 40 and SB 44 were evaluated for their ability to induce cytokines in peripheral blood mononuclear cells (PBMCs) by carrying out multiplex assays for 28 cytokines, IFN-α, IFN-β, IFN-γ, IL-1a, IL-1b, IL-1RA, IL-2, IL-3, IL-4, IL-5, IL-6, IL-7, IL-10, IL-12p40, IL-12p70, IL-13, IL-17A, TNFα, TNFβ, G-CSF, GM-CSF IL-8, MCP-1, Eotaxin, MIP-1α, MIP-1β, and RANTES. The compounds did not cause cytokine induction in human PBMC cultures up to 50 µM.

2). In order to evaluate whether SB 40 and SB 44 can augment the production of IFN in cells in the presence of bacterial nucleic acids, PBMCs were treated with BCG alone and using BCG with either SB 44 or SB 40 at 25 µM. BCG was used as a source of bacterial nucleic acids. PBMCs were incubated for 24 hrs with the compounds either alone or in the presence of BCG and the supernatants harvested. IFN levels were determined using ELISA. The compounds caused a modest augmentation of IFN production in the presence of BCG. (BCG did induce other cytokines such as IL-1, 6, 8, 10 and TNF-α from the same experiment).

3). Experiments were carried out to determine whether exogenous RIG-I and NOD2 expression can be induced in receptor-deficient cells using an ISG56 luciferase reporter. For this purpose PolyI-PolyC was used a positive control. Addition of SB 40 and SB 44 in these cells cause a modest 2-fold enhancement of ISG-56 expression over that induced by PolyI-PolyC due to the activation of RIG-I and NOD2.

The results demonstrate that induction of IFN (mediated through NOD2/RIG-I signaling cascade) by SB 40 and SB 44 can occur in the presence of foreign nucleic acids. There is hence less potential for these compounds to cause non-specific stimulation of immune pathways that would create a "cytokine storm" and associated systemic toxicity. These mechanisms of action observations are consistent with the adjuvant activity of SB 44 with BCG and should apply to ITS ISOMERS as well.

Example 8

Metabolism of SB 44 in S9 Fractions from Human Liver

SB 44 (10 µM) was incubated with a mix containing S9 fraction (pooled from human) (1 mg/ml), NADPH (1.3 mM) UDPGA (5 mM), Alamethicin (10 µg/ml) in 1 ml of 1×PBS buffer. S-(5'-adenosyl)-L-methionine iodide (0.1 mM), adenosine 3'-phosphate 5'-phosphosulfate lithium salt hydrate (0.1 mM) and acetyl CoA (1 mM). The metabolite samples were evaluated by HPLC and LC/MS analysis.

Exposure of the pro-drug $R_p$, $S_p$-SB 44 to liver microsomes up to eight hours resulted in its stereospecific conversion to the dinucleotide $R_p$, $S_p$-SB 40. LC/MS evaluation of the microsomal incubate revealed that the major product(s) of metabolism was the $R_p$, $S_p$-dinucleotide SB 40. A minor amount of the desulfurized product (<5%) was also detected as determined by MS analysis. A few minor metabolites (<10%) were also seen. However, the identity of these metabolites could not be firmly established based on molecular ion. In all cases, in the microsomal metabolism, both $R_p$-, and $S_p$ isomers of pro-drug SB 44 underwent stereospecific conversion to the active SB 40 with only minor amounts of desulfurized product [corresponding to SB 40] being observed. There were no significant rate differences in the conversion of the individual $R_p$- and $S_p$-isomers of SB 44 to $R_p$- and $S_p$-isomers of SB 40 respectively.

Similar to the serum-mediated conversion of SB 44 to SB 40, in the case of microsomes liver esterases appear to be the major metabolizing enzymes involved in the hydrolytic conversion of SB 44 to SB 40. In earlier bioreversibility studies of $R_p$-, $S_p$-SB 44 using serum, the individual isomers were stereospecifically converted to $R_p$-SB 44, $S_p$-SB 40 at almost equal rates. The *facile* bioconversion of SB 44 to SB 40 in liver and plasma is also consistent with broad substrate specificity of the ubiquitous esterase enzymes.

Example 9

In Vitro Metabolism of SB 44 by S9 Fractions

Similar to purified human liver microsomal studies, exposure of the prodrug SB 44 to human liver S9 fractions resulted in stereospecific conversion of SB 44 to the dinucleotide SB 40. Evaluation of the incubate by LC/MS revealed that besides the major product SB 40, minor amounts of the desulfurized product corresponding to SB 40 (<5%) were also formed. A few minor metabolites were also observed. The pattern of metabolites with the S9 fraction was similar to that observed with purified liver microsomes. Thus, there is no apparent evidence of any phase II conjugative reactions of SB 44 or that of the initially formed active metabolite SB 40.

Example 10

In Vitro Preclinical Toxicology Studies of SB 44

SB 44 was subjected to cytotoxicity evaluation against a panel of cell lines including Madin-Darby bovine kidney (MDBK), Vero, and HFF (human foreskin fibroblasts) to determine their $CC_{50}$. Standard Microculture Tetrazolium Assay (MTT) assays were performed in 96-well plates using MDBK, Vero, and HFF cell lines (obtained from American Type Cell Collection). Controls included the nucleoside analogs 3TC, AZT, and ddC, as well as media without drugs. SDS was used as a positive cytotoxic control. All prodrugs were tested in triplicate at concentrations of 100, 300, and 1000 µM. Following a 24-hour incubation of cells with the test substance, the MTT assay was carried out.

| Compound | Vero CC$_{50}$, µM | MDBK, CC$_{50}$, µM | HFF, CC$_{50}$, µM |
|---|---|---|---|
| SB 44 | >1000 | >1000 | >1000 |

The CC$_{50}$ of SB 40 was > 1000 µM.

Example 11

Bacterial Mutation Test (Screening Version) of SB 44

The purpose of this study was to evaluate the genotoxicity of the test article using the screening (non-GLP) version of the bacterial mutation test.

Study design: The test was performed on one occasion only. A subset of the standard tester strains (list strains) was used to evaluate the genotoxic potential of the test article.

The test article was formulated in dimethyl sulfoxide (DMSO) and tested at a maximum concentration of 5000 µg/plate (the standard limit dose for this assay) together with approximate half-log dilutions using the pre-incubation version of the bacterial mutation test. The absence of colonies on sterility check plates confirmed the absence of microbial contamination. The mean revertant colony counts for the vehicle controls were close to or within the laboratory historical control data. Appropriate positive control compounds (+/−S9 mix) induced increases in revertant colony numbers at least twice the concurrent vehicle control levels with the appropriate bacterial strain (1.5× for strain TA 100), confirming the sensitivity of the test system and activity of the S9 mix. No visible thinning of the background lawn of non-revertant bacteria was obtained following exposure to SB 44, indicating that the test article was non-toxic to the bacteria at the levels tested. No precipitation was observed.

No substantial increases in the revertant colony counts were obtained in any strain following exposure to the test article in either the absence or presence of S9 mix. It is therefore concluded that SB 44 did not show any evidence of genotoxic activity in this in vitro mutagenicity assay.

Example 12

In Vitro Cardiovascular Safety Assay (hERG Test)

The objective of this study was to examine the in vitro effects of SB 40 and SB 44 on the hERG (human ether-à-go-go-related gene) potassium channel current (a surrogate for IKr, the rapidly activating delayed rectifier cardiac potassium current).

In this study, hERG channels were expressed in a human embryonic kidney (HEK293) cell line that lacks endogenous IKr. HEK293 cells were stably transfected with hERG cDNA and the evaluations were done at room temperature using the QPatch HT®, an automatic parallel patch clamp system. Each test article was evaluated at 10, 50, 100 and 200 µM with each concentration tested in three cells (n=3). The duration of exposure to each test article concentration was 3 minutes.

The IC$_{50}$ values for both test articles could not be determined because the inhibition of hERG current by the highest concentration tested was less than 50%. The positive control E-4031, confirms the sensitivity of the test system to hERG inhibition.

In conclusion, SB 40 and SB 44 do not show any activity in the hERG assay and the IC50 is >200 µM.

Example 13

In Vivo Preclinical Toxicology Studies of SB 44

SB 44 is a mixture of two diastereomers (Rp,Sp) of which SB 1B is the Rp-isomer being present to the extent of 55-60% in the mixture. A number of preclinical studies were conducted by using SB 44 administered by oral gavage and study results are illustrative of possible outcome when SB 1B is used alone. The study has laid a firm foundation for preclinical studies with SB 1B since analytical and bioanalytical methodologies, formulation for toxicology studies, toxicology protocols, etc can be transferred to SB 1B.

Example 14

Dose Range-Finding Study of SB 44 in Sprague-Dawley Rats

The objective of this study was to determine potential toxic effects, to identify potential target organs of toxicity, and to determine a maximum tolerated dose (MTD) and a no observable adverse effect level (NOAEL) for the endpoints examined following daily oral gavage of SB 44 for 7 consecutive days to adult male and female Sprague-Dawley rats. Information from this study was used to design subsequent toxicity studies and determine the suitability of the proposed human dose. This study consisted of Phase A and Phase B. Phase A was a dose range-finding study. Two rats (1 male and 1 female) were included in the study. Animals were given a single dose of SB 44 at 1000 mg/kg by oral gavage (po) and observed for 3 days. Both animals had expected body weight gains and appeared normal throughout the study until their scheduled sacrifice. No necropsy was performed.

In Phase B, rats (3/sex/group) were given a daily oral dose of SB 44 at 50, 250, and 1000 mg/kg/day for 7 consecutive days. A control group (3/sex) was also given a daily oral dose of the vehicle, 50% PEG 400 plus 50% HPMCT (0.1% hydroxypropyl methylcellulose and 0.2% Tween 80 in sterile water), at an equivalent volume for 7 days. Animals were sacrificed on Day 8. The following parameters were evaluated: mortality/morbidity, clinical observations, body weights, clinical pathology (hematology and serum chemistry), organ weights, and, at necropsy, macroscopic observations and microscopic histopathology for liver tissues.

All animals in Phase B survived until their scheduled necropsy. A dose-dependent pattern of "shoveling" was noted in all animals in the treated groups, except males in the low dose group, on various days after dose administration. Because there were no other adverse signs related to neurological functions or other toxicology parameters, this observation most likely indicates that the rats perceived the taste and/or texture of the test article as unpleasant. No other drug-related effects were found for body weights, clinical pathology, organ weights, and macroscopic and microscopic evaluations. In conclusion, daily oral gavage administration of SB 44 to male and female Sprague-Dawley rats for 7 consecutive days produced no overt biologically or toxicologically significant adverse effects. The NOAEL is considered to be at least 1000 mg/kg/day when SB 44 is given by daily oral administration for 7 consecutive days.

Example 15

14-Day Toxicity Study of SB 44 in Rats with a Two-Week Recovery Period and Bone-Marrow Micronucleus Evaluation The objectives of this study were to determine potential toxic effects of SB 44 following daily oral dose administration for 14 days, and to evaluate the genotoxicity of SB 44 as determined by micronucleus evaluation. Male and female Sprague-Dawley rats were administered SB 44 daily at doses of 50, 200 and 500 mg/kg/day for 14 consecutive days. A satellite group was similarly treated for the purpose of toxicokinetic (TK) evaluations and plasma was analyzed for levels of SB 40, the active metabolite of SB 44. Micronucleus evaluations were performed to determine the potential genotoxicity of SB 44. Necropsies were performed on Day 15 for rats in the main study group and on Day 28 for rats in the recovery group.

All animals survived to the end of the study, SB 44 did not cause overt toxicity as determined by clinical observation, clinical pathology, body weight, urine parameters, necropsy and organ weight. Nevertheless, microscopic evaluation of tissues revealed changes in the thymus related to the test article. Minimal to mild increases in thymic phagocytic macrophages indicative of increased thymic lymphocyte destruction were observed in both males and females at 200 and 500 mg/kg/day. This change in thymus was present in both the main and recovery groups, but was not associated with any histopathological evidence of thymic atrophy or increased thymic involution. No evidence of increased lymphocyte destruction is present in other organs. This observation could be GI-stress related and is therefore considered to be of limited toxicological significance. In the micronucleus assay portion of this study, SB 44 was not found to induce micronuclei in rat bone marrow erythrocytes.

Example 16

Toxicokinetic Analysis

Only the maximal plasma concentration after oral administration ($C_{max}$) and area under the plasma concentration time curve up to the last sampling time point ($AUC_{last}$) were reported, as the majority of samples had SB 40 plasma concentrations at or near the LLOQ, making the determination of all TK parameters problematic. There was a nonlinear dose relationship for $C_{max}$ and $AUC_{last}$ in male and female rats on both Days 1 and 14. The highest systemic exposure was measured at the highest dose (500 mg/kg) for both males and females on Day 14, and Day 14 $C_{max}$ and $AUC_{last}$ values for SB 40 were higher than those on Day 1 for each dose administered. This accumulation of SB 40 after daily administration of SB 44 for 14 days may be caused by significant distribution to the liver combined with slow release back into the plasma. Females generally had greater systemic exposure than males, with the largest difference being about twofold on Day 14 in the 500 mg/kg dose groups. On the basis of the microscopic findings in the thymus and the absence of evidence of recovery from these effects of SB 44, the no observed effect level (NOEL) in this study was determined to be 50 mg/kg/day.

Example 17

Dose Range-Finding Study of SB 44 in Cynomolgus Monkeys

The objective of this study was to determine a maximum tolerated dose (MTD) and a no observable adverse effect level (NOAEL) for the endpoints examined following daily oral gavage of SB 44 for 4 consecutive days to cynomolgus monkeys. Information from this study was used to design subsequent dose-ranging toxicity studies and determine the suitability of the proposed human dose.

SB 44 was administered orally to cynomolgus monkeys consecutively for 4 days at 500 mg/kg/day. This dose was clinically well tolerated but was accompanied by elevations of ALT of about 2-fold and AST about 6-fold which returned to baseline about a week following cessation of treatment. All hematological parameters appeared normal and there was no evidence of other overt toxicity.

Conclusion: As mentioned before, SB 44 is a mixture of two isomers (Rp,Sp) of which SB 1B is the Rp-isomer being present at greater than 55%. SB 1B appears more efficacious as an adjuvant than SB 44 in the short-term primary and long-term Mtb challenge experiments in mice. Also, not much is known about the efficacy of the second isomer (Sp-isomer) of SB 44 as adjuvant. A number of preclinical studies were conducted by using SB 44. The study results are illustrative of excellent safety for the dinucleotide composition represented by SB 44. Consequently, it is anticipated an excellent safety profile for subcutaneously administered SB 1B.

Example 18

Induction of Interferon in PBMCs Treated with the BCG and Compounds

Figure 17:
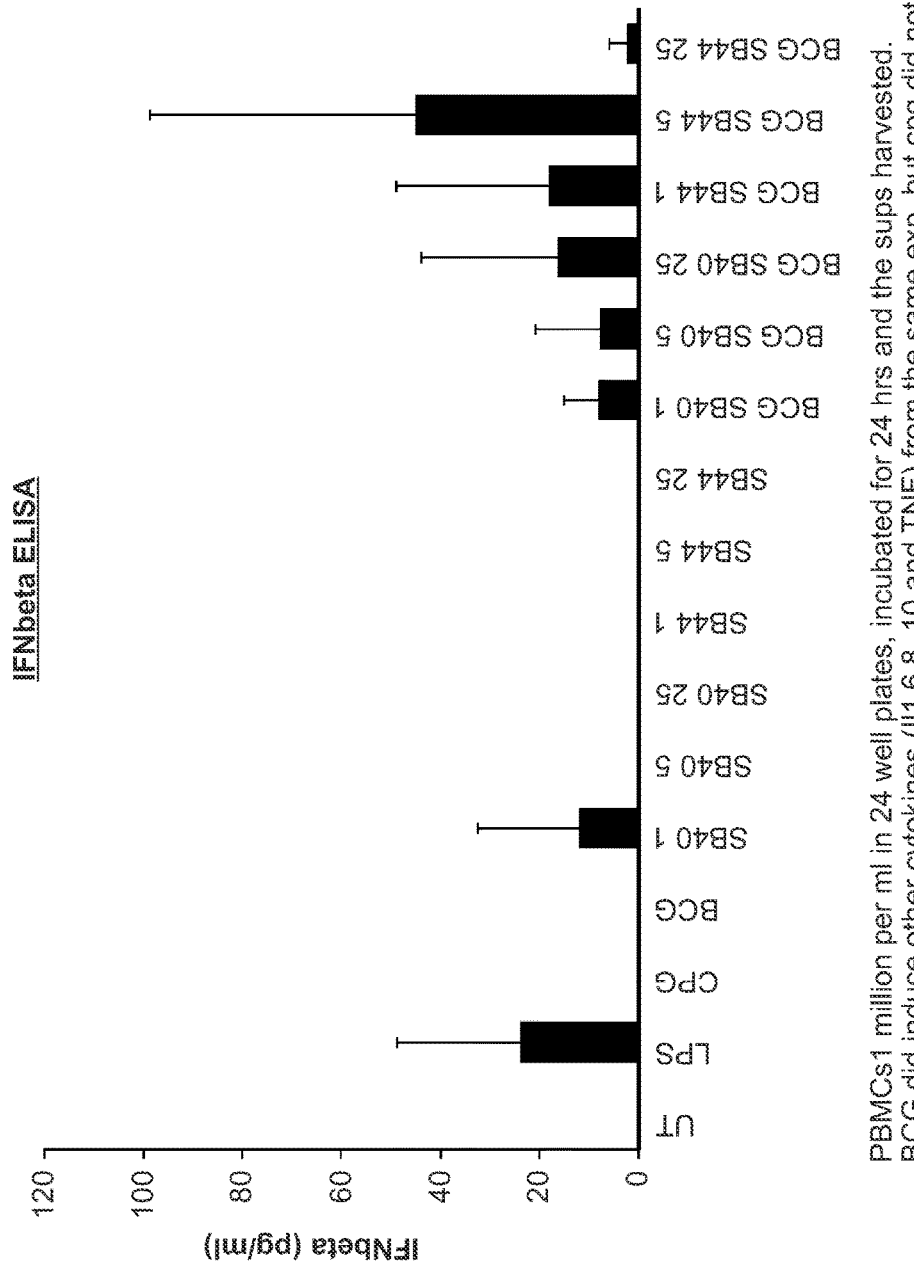
FIG. 17 shows the induction of interferon in PBMCs treated with the BCG when combined with the compounds of the invention.

For this assay, PBMCs were plated at 1 million cells per ml in 24 well plates. Groups of plates were treated with BCG, BCG+ compounds, and incubated for 24 hrs. The cells were lysed and the supernatants harvested. The production of cytokines and type I Interferon was assessed using the ELISA assay with standard kits. BCG did induce other cytokines (IL-1, IL-6, IL-8, IL-10 and TNF) from the same experiment. Cells treated with BCG and compounds induced increased production of IFN compared to BCG alone. The results are provided in FIG. 17.

BCG did induce other cytokines (IL-1, IL-6, IL-8, IL-10 and TNF) from the same experiment. Cells treated with BCG and compounds induced increased production of IFN compared to BCG alone.

In summary, the compounds claimed in this invention act as activators of intracellular microbial sensors and cause activation of immune response. When used in conjunction with vaccines, the compounds acted as adjuvants and potentiate the immune response induced by vaccines.

Example 19

In Vitro Cytotoxicity Studies

In vitro cytotoxicity studies of the lead(s) using a panel of cell lines predictive of liver, kidney, bone marrow and mitochondrial toxicity (in-house).

The compounds 1 and 3 have excellent safety profile with $CC_{50}$>1000 micromolar in a number of cell lines. Standard MTT assays were performed in 96-well plates using the Promega CellTiter96 Non-radioactive Cell Proliferation Assay Kit in conjunction with a 96-well Plate Reader (ThermoMax, Molecular devices), and MDBK, Vero, and HFF cell lines (obtained from ATCC). Several controls were employed including the nucleoside analogs 3TC, AZT, and ddC, as well as, media without drugs. SDS was used as a positive cytotoxic control. The compounds were tested in triplicate at concentrations of 100, 300, and 1000 µM. Following a 24-hour incubation of cells with the test substance, the MTT assay was carried out. All the tested compounds showed CC50>1000 micromolar indicating high safety index for the compounds.

REFERENCES CITED 1. (a) *WHO REPORT*: Global prevalence of hepatitis A, B, C. Weekly Epidemiological Record, Vol 77, 6, 2002; (b) Delwaide, J., Gerard, C. *Evidence-based medicine treatment of chronic hepatitis C. Liege study Group on Viral hepatitis*. Revue medicale de Liege 55, 337, 2000.
2. (a) Sorrell, M. F., Belongia, E. A., Costa, J., Gareen, I. F., Grem, J. L., Inadomi, J. M., Kern, E. R., McHugh, J. A., Peterson, G. M., Rein, M. F., Strader, D. B., Trotter, H. T. *National Institutes of Health Consensus Development Conference Statement: Management of Hepatitis B. Ann. Int. Med.* 150, 204, 2009.
(b) Wild, C. P., Hall, A. J. *Primary prevention of hepatocellular carcinoma in developing countries. Mutation Res.* 462, 381, 2000. Liang, T. J., Rehermann, B., Seeff, L. B., Hoofnagle, J. H. *Pathogenesis, natural history, treatment, and prevention of hepatitis C. Ann. Intern. Med.* 132, 296, 2000.
3. Akira, S., Uematsu, S., Takeuchi, O. Pathogen recognition and Innate immunity. Cell, 24, 783-801, 2006.
4. Katze, M. G., He, Y., Gale, M. Viruses and interferon: A fight for supremacy. Nature Reviews, 2, 675, September 2002.
5. Takeda, K., Akira, S. Toll-like receptors in innate immunity. International Immunology, 17, 1-14, 2005.
6. Saito, T., Hirai, R., Loo, Y-M., Owen, D., Johnson, C. L., Sinha, S. C., Akira, S., Fujita, T., Gale, M. Regulation of innate antiviral defenses through a shared repressor domain in RIG-I and LGP2. Proc. Natl. Acad. Sci. USA, 10, No. 2, 582-587, 2007.
7. Meylan, E., Curran, J., Hofmann, K., Moradpour, D., Binder, M., Bartenschlager, R., Tschopp, J. Cardif is an acceptor protein in the RIG-I antiviral pathway and is targeted by hepatitis C virus. Nature, 437, 1167-1172, 2005.
8. Hiscott, J., Lin, R., Nakhaei, P., Paz, S. MasterCARD: A priceless link to innate immunity. TRENDS in Molecular Medicine, 12, 53-56, 2006.
9. Cui, S., Eisenacher, K., Kirchhofer, A., Brozka, K., Lammens, A., Lammens, K., Fujita, T., Conzelmann, K-K., Krug, A., Hopfner, K-P. The C-terminal regulatory domain is the RNA 5'-triphosphate sensor of RIG-I. Molecular Cell, 29, 169-179, 2008.
10. Yoneyama, M., Kikuchi, M., Natsukawa, T., Shinobu, N., Imaizumi, T., Miyagishi, M., Taira, K., Akira, S., Fujita, T. The RNA helicase RIG-I has an essential function in double-stranded RNA-induced innate antiviral responses. Nat. Immunol. 5, 730-737, 2004.
12. Hornung, V., Ellegast, J., Kim, S., Brzozka, K., Jung, A., Kato, H., Poeck, H., Akira, S., Conzelmann, K-K., Schlee, M., Endres, S., and Hartmann, G. 5'-triphosphate RNA is the ligand for RIG-I. Science, 314, 994-997, 2006.
13. Pichlmair, A., Schulz, O., Tan, C. P., Naslund, T. I., Liljestrom, P., Weber, F., Reis e Sousa, C. RIG-I mediated antiviral responses to single-stranded RNA bearing 5'-phosphates. Science, 314, 997-1001, 2006.
14. Myong, S., Cui, S., Cornish, P. V., Kirchhofer, A., Gack, M. U., Jung, J. U., Hopfner, K-P., Ha, T. Cytosolic viral sensor RIG-I is a 5'-triphosphate-dependent translocase on double-stranded RNA. Science, 323, 1070, 2009.
15. Gack, M. U., Kirchhofer A., Shin, Y. C., Inn K. S., Liang C., Cui S., Myong S., Ha T., Hopfner, K-P., Jung, J. U. Roles of RIG-I N-terminal tandem CARD and splice variant in TRIM25-mediated antiviral signal transduction. Proc Natl Acad Sci USA. 105(43): 16743-8, 2008.
15. (a) Sabbah, A., Chang, T. H., Harnack, R., Frohlich, V., Tominaga, K., Dube, P. H., Xiang, Y., Bose, S. Activation of innate immune antiviral responses by NOD2. Nat. Immunol. 10, 1073, 2009. (b) Franchi, L., Warner, N., Viani, K., Nuñez, G. Function of NOD-like receptors in microbial recognition and host defense. Immunol. Rev. 227, 106, 2009.
16. (a) Iyer, R. P., Pandey, R., Kuchimanchi, S. RNA interference: An exciting new approach for target validation, gene expression analysis and therapeutics. Drugs of the Future, 2003, 28, 51-59. (b) For reviews on antisense approach see: (i) Mirabelli, C. T., Crooke, S. T. Antisense Oligonucleotides in the context of modern molecular drug discovery and development. In: Antisense Research and Applications, S. T. Crooke and B. Lebleu (Eds.,) CRC Press, New York 1993, 7-35. (ii) Szymkowski, D. E. Developing antisense oligonucleotides from the laboratory to clinical trials. Drug. Disc. Today, 1996, 1, 415-28
17. Iyer, R. P., Jin, Y., Roland A., Money, J. D., Mounir, S., Korba, B. E. Phosphorothioate Di- and Tri-nucleotides as a novel class of anti-HBV agents. Antimicrob. Agents Chemother. 48(6): 2199-2205, 2004.
18. Iyer, R. P., Roland A., Jin, Y., Mounir, S., Korba, B. E., Julander, J., Money, J. D. Anti-hepatitis B virus activity of ORI-9020, a novel phosphorothioate dinucleotide, in a transgenic mouse model. Antimicrob Agents Chemother. 48(6):2318-20, 2004.
19. For examples of nucleotide combinatorial synthesis and antiviral evaluation, see: (a) Jin, Y., Roland, A., Zhou, W., Fauchon, M., Lyaku, J., Iyer, R. P. Bioorg. Med. Chem. Lett. 10, 1921-25, 2000. (b) Jin, Y., X. Chen, M.-E. Cote, A. Roland, B. Korba, S. Mounir, Iyer, R. P. Bioorg. Med. Chem. Lett. 11, 2057-2060, 2001.
20. Iyer, R. P., Coughlin, J., Padmanabhan, S. Microwave-assisted functionalization of solid supports for rapid loading of nucleosides. Current Protocols Unit 3.13, (Beaucage et al Eds) John Wiley and Sons, 2006.
21. Padmanabhan, S., Coughlin, J., Iyer, R. P. Microwave-assisted functionalization of solid supports. Application in the rapid loading of nucleosides on controlled-pore-glass (CPG). Tet. Lett. 46, 343-347, 2005.
22. Iyer, R. P., Coughlin, J., Padmanabhan, S. Rapid functionalization and loading of solid supports. Organic Preparations & Procedure International, 37, 205-212, 2005.

What is claimed:
1. A method of improving an immune system response in a subject against a tuberculosis infection, said method comprising
    administering to the subject a BCG vaccine; and
    administering to the subject an effective amount of a vaccine adjuvant of formula (II):

43

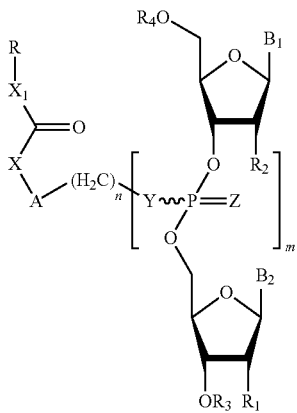

II or a pharmaceutically acceptable salt, racemate, enantiomer, diastereomer, geometric isomer, or tautomer thereof, wherein
X is absent, O, NH, NR, or S;
$X_1$ absent, O, or NH;
A is absent, aryl, or aralkyl;
n is 0, 1, 2, 3, 4, or 5;
R is alkyl, substituted alkyl, cycloalkyl, aryl, substituted aryl, aralkyl, heterocyclic, O-alkyl, O-heteroaryl, or steroidal;
$R_1$ and $R_2$ are each independently, H, OH, O-alkyl, alkyl, substituted alkyl, cycloalkyl, aryl, substituted aryl, aralkyl, heterocyclic, O-aryl, O-heteroarylaryl, or heterocyclic;
$R_3$ is selected from H, alkyl, substituted alkyl, C(O)-alkyl, C(O)O-alkyl, C(O)-aryl, C(O)O-aryl, C(O)NH-alkyl, and C(O)NH-aryl;
Y and Z are each independently O or S;

44

$B_1$ and $B_2$ are each independently adenine, guanine, thymine, cytosine, uracil, or a modified nucleoside;
m is 1, 2, 3, 4, 5, or 6;
$R_4$ is independently H, alkyl, substituted alkyl, C(O)-alkyl, C(O)O-alkyl, C(O)-aryl, C(O)O-aryl, C(O)NH-alkyl, C(O)NH-aryl, or a monophosphate, diphosphate, or triphosphate group.

2. The method of claim 1, wherein said vaccine adjuvant is a compound of the following structure:

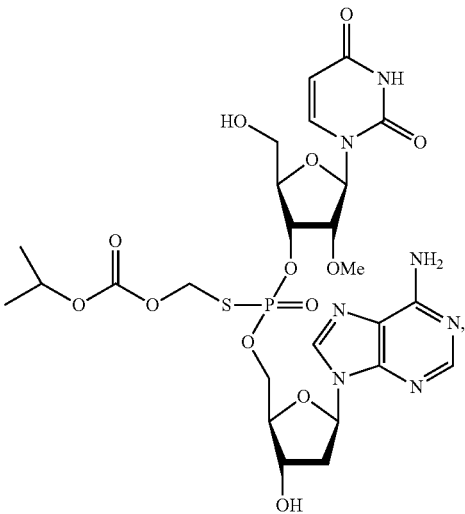

or a pharmaceutically acceptable salt, racemate, enantiomer, diastereomer, geometric isomer, or tautomer thereof.

* * * * *

UNITED STATES PATENT AND TRADEMARK OFFICE
CERTIFICATE OF CORRECTION

PATENT NO.        : 10,391,166 B2
APPLICATION NO.   : 14/767113
DATED             : August 27, 2019
INVENTOR(S)       : Radhakrishnan P. Iyer It is certified that error appears in the above-identified patent and that said Letters Patent is hereby corrected as shown below:

On the Title Page

Item (73) Assignee: delete "SPRING BREAK PHARMACEUTICALS, INC." and replace with
-- SPRING BANK PHARMACEUTICALS, INC. --.

Signed and Sealed this
Thirty-first Day of December, 2019

Andrei Iancu
*Director of the United States Patent and Trademark Office*